US009387170B2

(12) United States Patent
Ishii et al.

(10) Patent No.: US 9,387,170 B2
(45) Date of Patent: *Jul. 12, 2016

(54) DRUG HAVING REGULATORY CELL LIGAND CONTAINED IN LIPOSOME

(71) Applicant: RIKEN, Saitama (JP)

(72) Inventors: Yasuyuki Ishii, Yokohama (JP); Risa Nozawa, Yokohama (JP); Masaru Taniguchi, Yokohama (JP)

(73) Assignee: RIKEN, Saitama (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/540,235

(22) Filed: Nov. 13, 2014

(65) Prior Publication Data

US 2015/0071991 A1    Mar. 12, 2015

Related U.S. Application Data

(60) Continuation of application No. 12/687,428, filed on Jan. 14, 2010, now Pat. No. 8,920,774, which is a division of application No. 11/634,161, filed on Dec. 6, 2006, now abandoned, which is a continuation of application No. PCT/JP2005/010254, filed on Jun. 3, 2005.

(30) Foreign Application Priority Data

Jun. 11, 2004 (JP) ................... 2004-173844
Oct. 28, 2004 (JP) ................... 2004-313830

(51) Int. Cl.
*A61K 45/00* (2006.01)
*A61K 9/127* (2006.01)
*A61K 31/4745* (2006.01)
*A61K 31/728* (2006.01)
*A61K 31/7088* (2006.01)
*A61K 31/7032* (2006.01)

(52) U.S. Cl.
CPC ............. *A61K 9/127* (2013.01); *A61K 31/4745* (2013.01); *A61K 31/7032* (2013.01); *A61K 31/7088* (2013.01); *A61K 31/728* (2013.01)

(58) Field of Classification Search
CPC .................................................... A61K 9/127
See application file for complete search history.

(56) References Cited

U.S. PATENT DOCUMENTS

| 4,416,872 | A | 11/1983 | Alving et al. | |
| 5,043,165 | A | 8/1991 | Radhakrishnan | |
| 5,861,520 | A | 1/1999 | Ogawa et al. | |
| 6,492,337 | B1 | 12/2002 | Fredman et al. | |
| 6,747,010 | B2 | 6/2004 | Taniguchi et al. | |
| 2002/0031787 | A1 | 3/2002 | Maclaren et al. | |
| 2002/0115624 | A1* | 8/2002 | Behar | A61K 31/7028 514/42 |
| 2003/0157135 | A1 | 8/2003 | Tsuji et al. | |
| 2003/0194391 | A1 | 10/2003 | Ashman et al. | |
| 2004/0253574 | A1 | 12/2004 | Schuler et al. | |
| 2006/0116331 | A1 | 6/2006 | Jiang et al. | |

FOREIGN PATENT DOCUMENTS

| CA | 2500478 | 4/2004 |
| JP | 1-93562 | 4/1989 |
| JP | H06-157335 | 6/1994 |
| JP | 8-048658 | 2/1996 |
| JP | H08-116971 | 5/1996 |
| JP | 11-302155 | 11/1999 |
| JP | 2002-369639 | 12/2002 |
| JP | 2004-507238 | 3/2004 |
| WO | WO 98/43616 | 10/1998 |
| WO | WO 99/33475 | 7/1999 |
| WO | WO 02/070711 | 9/2002 |
| WO | WO 02/080952 | 10/2002 |
| WO | WO 03/009812 | 2/2003 |
| WO | WO 2004/032969 | 4/2004 |

OTHER PUBLICATIONS

Dale I. Godfrey, "Going Both Ways: Immune Regulation via CD1d-depenedent NKT Cells," *The Journal of Clinical Investigation*, vol. 114, No. 10 (Nov. 2004). pp. 1379-1388.
Aki Ishikawa, et al., "A Phase I Study of α-Galactosylceramide (KRN7000)—Pulsed Dendritic Cells in Patients with Advanced and Recurrent Non-Small Cell Lung Cancer," *Clinical Cancer Research*, 2005, 11: 1910-1917.
Rachel D. Kuns, et al., "Invariant Natural Killer T Cell-Natural Killer Cell Interactions Dictate Transplantation Outcome After α-galactosylceramide Administration," *Blood*, 113: 5999-6010 (2009).
Stedman's Medical Dictionary, pp. 322, 1669, 1670 (2th Ed. 2000).
Suzuki et al., *Cancer Research*, vol. 64, pp. 8754-8760 (2004).
Suzuki et al., "Liposome-Encapsulated CpG Oligodeoxynucleotides as Potent Adjuvant for Inducing Type I Innate mmunity" *Cancer Research*, vol. 64, No. 23, Dec. 1, 2004, pp. 8754-8760.
Fick Jr., et al., "Immunotherapy Approach to Allergic Disease," *Immunopharmacology*, vol. 48, pp. 307-310, (2000).
Toda et al., "Inhibition of Immunoglobulin E Response to Japanese Cedar Pollen Allergen (Cry j 1) in Mice by DNA Immuniaztion: Different Outcomes Dependent on the Plasmid DNA Inoculation Method," *Immunology*, vol. 99, pp. 179-186 (2000).
Kim et al., "An Ovalbumin-IL-12 Fusion Protein is more Effective than Ovalbumin Plus Free Recombinant IL-12 in Inducing a T Helper Cell Type 1-Dominated Immune Response and Inhibiting Antigen-Specific IgE Production, " *The Journal of Immunology*, pp. 4137-4144, (1997).
Morecki et al., *Experimental Hematology*, pp. 630-637 (2004).
Seino et al., *Transplantation Proceedings*, vol. 33, Issues 1-2, pp. 437-438 (2001).
Junqing Cui et al., *Science*, 278: 1623-26 (Nov. 28, 1997).

(Continued)

*Primary Examiner* — Albert Navarro
(74) *Attorney, Agent, or Firm* — Oblon, McClelland, Maier & Neustadt, L.L.P.

(57) ABSTRACT

A liposome containing a regulatory cell ligand such as α-galactosyl ceramide or β-galactosyl ceramide is employed as the active ingredient of a drug for preventing or treating immune diseases etc.

6 Claims, 21 Drawing Sheets

(56) References Cited

OTHER PUBLICATIONS

Duramad et al., *Biol. Blood Marrow Transplant*, 17 (8), pp. 1154-1168 (Aug. 2011).
Haraguchi et al., *J. Immunology*, 175: 1320-1326 (2005).
Hashimoto et al., *J. Immunology*, 174: 551-556 (2005).
Holler et al., *Bone Marrow Transplant*, 25 (3): 237-41 (Feb. 2000).
Ishii et al., *Frontiers in Bioscience*, 13: 6214-6228 (May 1, 2008).
Kawano et al., *Science*, 278: 1626-29 (Nov. 28, 1997).
Shimosaka, *Int. J. Hematol*, 76 Suppl. 1:277-9, Abstract (Aug. 2002).
Sonoda et al., *J. Immunology*, 166: 42-50 (2001).
Tasahiro et al., *Trends in Glycoscience and Glycotechnology* (Minireview), 22 (128): 280-295 (Nov. 2010).
Zhong et al., *J. Exp. Medicine*, 186(5): 673-682 (Aug. 29, 1997).
Examiner's Report dated Feb. 28, 2012, corresponding with Canadian Patent Application No. 2,569,590.
Office Action, corresponding with Japanese Patent Application No. 2006-514482 dated Mar. 8, 2011.
*Journal of Neuroimmunology*, vol. 28, pp. 119-130 (1990).
Berson et al., "Interaction of Human immunodeficiency Virus Type I Envelope Protein with Lipsomes Containing Galactosylceramide,k" *Perspective in Drug Discovery and Design*, vol. 5, No. 0; (1966), pp. 169-180.
Seki et al., "The Liver as a Crucial Organ in the First Line of Hose Defense: The Roles of Kupffer Cells, Natural Killer (NK) Cells and NK1.1 Ag+ Cells in T Helper 1 Immune Responses," *Immunological Reviews*, vol. 174, pp. 35-46 (2000).
Watanabe et al., "Relationships Between Intermediate TCR Cells and NK 1.1+ T Cells in Various Immune Organs," *The Journal of Immunology*, pp. 2972-2983 (1995).
Sumuda et al., "Selective Reduction of T Cells Bearing Invariant Vα24JαQ Antigen Receptor in Patients with Systematic Sclerosis," *J. Exp. Med.*, vol. 182, pp. 1163-1168 (1995).
Nakayama et al., "The Role of a α-Galatosylceramide-Activated Vα14 Natural Killer T Cells in the Regulation of Th2 Cell Differentiation," *Int'l Arch Allergy Immunol*, vol. 124, pp. 38-42 (2001).
Cui et al., "Inhibition of T Helper Cell Type 2 Cell Differentiation and Immunoglobulin E Response by Ligand-Activated Vα14 Natural Killer T Cells," *J. Exp. Med.*, vol. 190, No. 6, pp. 783-792 (Sep. 20, 1999).
Hong et al., "The Natural Killer T-Cell Ligand α-Galactosylceramide Prevents Autoimmune Diabetes in Non-Obese Diabetic Mice," *Nature Medicine*, vol. 7, N. 9, pp. 1052-1056 (Sep. 2001).
Svennerholm et al., "Sphingolipids of Human Skeletal Muscle," *Biochim. Biophys, Acta*, vol. 280, pp. 626-636 (1972).
Karlsson et al., "The Sphingolipid Composition of Bovine Kidney Cortex, Medulla and Papilla," *Biochimica et Biophysica Acta*, vol. 316, pp. 316-335 (1973).
Motoki et al, "Immunostimulatory and Antitumor Activities of Monoglycosylceramides having Various Sugar Moieties," *Biol. Pharm. Bull.*, vol. 18, No. 11, pates 1487-1497, (1995).
Zheng et al., "Cutting Edge: A Role for CD1 in the Pathogenesis of Lupus in NZB/NZW Mice, " *The Journal of Immunology*, pp. 5000-5004 (2000).
Pal et al., "Costimulation-Dependent Modulation of Experimental Autoimmune Encephalomyelitis by Ligand Stimulation of Vα14 KT Cells," *The Journal of Immunology*, pp. 662-668 (2001).
Singh et al., "Natural Killer T Cell Activation Protects Mice Against Experimental Autoimmune Encephalomyelitis," *J. Exp. Med.*, vol. 194, No. 12, pp. 1801-1811 (Dec. 17, 2001).
Miyamoto, et al., "A Synthetic Glycolipid Prevents Autoimmune Encephalomyelitis by Inducing $T_H2$ Bias of Natural Killer T Cells," *Nature*, vol. 413, pp. 531-534, (Oct. 4, 2001).
Stein et al., "Treatment of Spinal Cord-Induced Experimental Allergic Encephalomyelitis in the Lewis Rat with Liposomes Presenting Central Nervous System Antigens," *Journal of Neuroimmunology*, vol. 28, pp. 119-130 (1990).
Long et al., "Characterization of Human Immunodeficiency Virus Type 1 gp120 Binding to Liposomes Containing Galactosylceramide," *Journal of Virology*, vol. 68, No. 9, pp. 5890-5898. (Sep. 1994).
Morita et al., "Structure-Activity Relationships of α-Galactosylceramides Against B26-Bearing Mice," *J. Med. Chem.*, vol. 38, pp. 2176-2187.
Shimosaka et al., "Role of NKT Cells and α-Galactosyl Ceramide," *International Journal of Hematology*, pp. 277-279 (Aug. 2002).
International Search Report issued Jul. 26, 2005, in corresponding International Patent Application PCT/JP2005/010254.
The American Heritage Dictionary of the English Language; (online). Definition of sphingosine, https://www.ahdictionary.com/word/search.html?q=sphingosine&submit.x=34 &submit.y=18 (Feb. 17, 2016).

\* cited by examiner

DRUG HAVING REGULATORY CELL LIGAND CONTAINED IN LIPOSOME

This application is a Continuation application of U.S. Ser. No. 12/687,728, filed Jan. 14, 2010, now allowed; which is a Divisional application of U.S. application Ser. No. 11/634,161, filed Dec. 6, 2006, now abandoned; which is a Continuation application of PCT/JP2005/010254, filed Jun. 3, 2005; and claims priority to Japanese Patent Application No. 2004-173844, filed Jun. 11, 2004; and Japan Patent Application No. 2004-313830, filed Oct. 28, 2004, all incorporated herein by reference.

TECHNICAL FIELD

The present invention relates to a drug having a regulatory cell ligand contained in a liposome, and more particularly relates to a drug for immune diseases such as allergic diseases and autoimmune diseases.

BACKGROUND ART

Immune diseases such as allergic diseases, autoimmune diseases and graft-versus-host diseases (GVHD) are the disease caused by abnormality or incompatibility of the immune system. Among them, patients with some illness of allergic disease tend to increase year by year, and it has been reported that 70% of Japanese people have already affected with some allergic disease. A category of the allergic diseases is broad and includes asthma, atopic dermatitis, pollinosis, food allergy and allergodermia. Many of the patients with allergy are known to develop various allergic diseases sequentially, which is referred to as allergy march. In recent years in Japan, the patients with pollinosis or pediatric atopic asthma complicated with allergic rhinitis or allergic conjunctivitis have increased markedly. As a reason for this, it has been thought that change of life environment, particularly the change of immunological environment (decrease of bacterial infection, increase of house dust density in an airtight house) in infant in which the immune system is formed may increase the production of IgE antibody. It is evident that narrowly defined allergic diseases such as allergic rhinitis, allergic conjunctivitis and atopic asthma are caused by type I allergic reaction in which the IgE antibody and Th2 cells which induce the production of the antibody are involved. It has been frequently reported that the IgE antibody and the predominant Th2 cells are deeply involved during the stage of occurrence of other various allergic diseases other than them. From the above, it is predicted that depressed production of the IgE antibody which is responsible for the type I allergic reaction and inhibition of Th2 cell differentiation can be promising procedures for therapy of the allergic diseases. For the patients with allergic disease predicted to further increase in the future, a causal therapy by medicaments made based on allergy occurrence mechanisms or a preventive (vaccine) method which reduces the allergy from occurring are thought to be somehow effective. It is necessary to assure high safety profile (low side effect) for remedy.

A humanized anti-IgE antibody (rhuMAb-E25, Genentech Inc.) has been shown to be highly effective in clinical trials with the patients with atopic asthma (see Non-patent literature 1). In an attempt to inhibit the production of an antigen specific IgE antibody using an artificial compound, an immune response of Th1 type was induced in BALB/c mice immunized with a plasmid DNA in which cedar pollen antigen Cry j1 gene had been incorporated. As a result, an IgG2a antibody was produced, and even when the Cry j1 antigen and alum were boosted, the production of IgG1 and IgE antibodies was suppressed (see Non-patent literature 2). When the mouse was immunized with an OVA-IL-12 fusion protein, the immune response of OVA specific Th1 type was induced. Its efficiency was much higher than in the case of being immunized with a mixture solution of OVA and IL-12, and the OVA specific IgG2a antibody was produced (see Non-patent literature 3). This report indicates that the response can be biased to the Th1 type by the immunization with a complex of the antigen and a cytokine inducer and along with it the antigen specific production of the IgE antibody can be suppressed.

To prevent the allergic disease or lead it to cure, it can be an effective procedure to control regulatory cells which suppress the differentiation, proliferation and functions of Th cells and IgE antibody producing B cells. An NKT cell is believed to be one of the regulatory cells which plays an important role in cancer cells, parasites and protozoa, and for eliminating intracellularly infected bacteria such as Listeria and tuberculosis germs (see Non-patent literature 4). It has been demonstrated that the NKT cell is an intermediate TCR cell ($TCR_{int}$ cell) which expresses a T cell receptor (TCR) moderately, and is the cell analogous to an Natural Killer (NK) cell in points of exhibiting a large granular lymphocyte (LGL)-like morphology, constitutively expressing IL-2R β chain on the surface and having perforin granules, but is absolutely different from the NK cell in point of having TCR (see Non-patent literature 5). A $V\alpha14^+$ NKT cell is one of subsets of the above NKT cells, many of the $V\alpha14^+$ NKT cells express Vα14Jα281 mRNA and have this as TCR α chain. A Vα24JaQ chain, a human homolog which is homologous to the murine Vα14Jα281 chain is present at 20 to 50% in peripheral blood $CD4^-/CD8^-$ T cells in healthy donors (see Non-patent literature 6).

α-Galactosyl ceramide which is a ligand compound of these NKT cells induces the cytokine production of both IFN-γ and IL-4. Thus, it has been shown that the NKT cell is the regulatory cell for the differentiation of Th1/Th2 (see Non-patent literature 7). When α-galactosyl ceramide was administered to C57BL/6 mice, the production of IgE antibody induced by DNP-OVA and alum was inhibited. In the same experiment using mice deleting the Vα14-NKT cells, the production of IgE antibody was not inhibited (see Non-patent literature 8). In the experiments in which α-galactosyl ceramide compound was administered to NOD mice, a type I diabetes model, the symptomatic improvement was observed. Thus, the possibility has been suggested that the Vα14-NKT cell augments the immune response via Th2 cells (see Non-patent literature 9). However, the effect obtained by α-galactosyl ceramide compound alone is limited, and further improvement of medicinal efficacy has been required.

Meanwhile, substances of β-galactosyl ceramide and β-glycosyl ceramide are present in vivo, but it has been shown that they have much lower activity compared with immunopotentiation and anti-tumor effects of α-galactosyl ceramide compound (see Non-patent literatures 10 to 12, and Patent document 1).

Additionally, the NKT cell has been known to effectively serve for autoimmune diseases (see Non-Patent literatures 13 to 16). Therefore, if immunosuppressive functions, e.g., the production of IL-10 in the NKT cells can be selectively augmented, it is thought to be effective for the treatment of not only the allergic diseases but also the other immune diseases such as autoimmune diseases and GVHD. However, no ligand which alone can selectively augment the immunosuppressive function of the NKT cell has been known. No liposome has been used for such a purpose.

Patent document 1: JP Hei-1-93562 A, Publication;
Non-patent literature 1: Immunopharmacology, 48:307 (2000);
Non-patent literature 2: Immunology, 99:179(2000);
Non-patent literature 3: J. Immunol., 158:4137 (1997);
Non-patent literature 4: Clin. Immunol., 28, 1069 (1996);
Non-patent literature 5: J. Immunol., 155, 2972 (1995);
Non-patent literature 6: J. Exp. Med., 182, 1163(1995);
Non-patent literature 7: Nakayama. T., et al., Int. Arch. Allergy Immunol., 124:38-42 (2001);
Non-patent literature 8: J. Exp. Med., 190, 783-792, (1999);
Non-patent literature 9: Nat. Med., 7:1052-1056 (2001);
Non-patent literature 10: Biochem. Biophys. Acta, 280, 626 (1972);
Non-patent literature 11: Biochem. Biophys. Acta, 316, 317 (1973);
Non-patent literature 12: Biol. Pharm. Bull., 18, 1487 (1995);
Non-patent literature 13: J. Exp. Med., 186:677 (1997);
Non-patent literature 14: J. Immunol., 166:62 (2001);
Non-patent literature 15: J. Exp. Med., 194:1801 (2001); and
Non-patent literature 16: Nature, 413:531(2001).

DISCLOSURE OF INVENTION

It is an object of the present invention to provide a drug targeting a regulatory cell in vivo, mainly a drug for immune diseases including but not limited to allergic diseases and autoimmune diseases.

The present inventors have found that a composition having a regulatory cell ligand such as β-galactosyl ceramide and α-galactosyl ceramide compounds contained in a liposome has an inducible action of IL-10-producing T cells and an inhibitory action on IgE antibody production which are not exerted by a solution of these compound alone and is effective as a preventive or therapeutic agent for the immune diseases such as allergic diseases. The present inventors have further found that a composition having α-galactosyl ceramide contained in a liposome can inhibit differentiation and proliferation of pathogenic T cells by selectively augmenting immunosuppressive functions of NKT cells and thus is effective as a preventive or therapeutic agent for autoimmune diseases and graft-versus-host disease, and have completed the present invention.

That is, the present invention is as follows.

[1] Drugs comprising a liposome containing a regulatory cell ligand, as an active ingredient.

[2] The drugs of [1] wherein the regulatory cell is an NKT cell.

[3] The drugs of [1] or [2] wherein the regulatory cell ligand is β-galactosyl ceramide substances.

[4] The drugs of [1] or [2] wherein the regulatory cell ligand is α-galactosyl ceramide substances.

[5] The drugs of any of [1] to [4] wherein the liposome further contains CpG oligonucleotide or imiquimod.

[6] The drugs of any of [1] to [5] wherein the liposome further contains one or more selected from the group consisting of allergens, autoantigens and derivatives thereof, which derivatives are antigens having one or more T cell epitopes.

[7] The drugs of any of [1] to [6] which is a preventive agent or a therapeutic agent for immune diseases.

[8] The drugs of [7] wherein the immune diseases are allergic diseases.

[9] The drugs of [8] wherein the allergic diseases are atopic bronchial asthma, allergic rhinitis, pollinosis or atopic dermatitis.

[10] The drug of [4] which is a preventive agent or a therapeutic agent for autoimmune diseases or graft-versus-host disease.

[11] A regulatory cell-inducing agent comprising a liposome containing a regulatory cell ligand, as an active ingredient.

MODES FOR CARRYING OUT THE INVENTION

Figure 1:
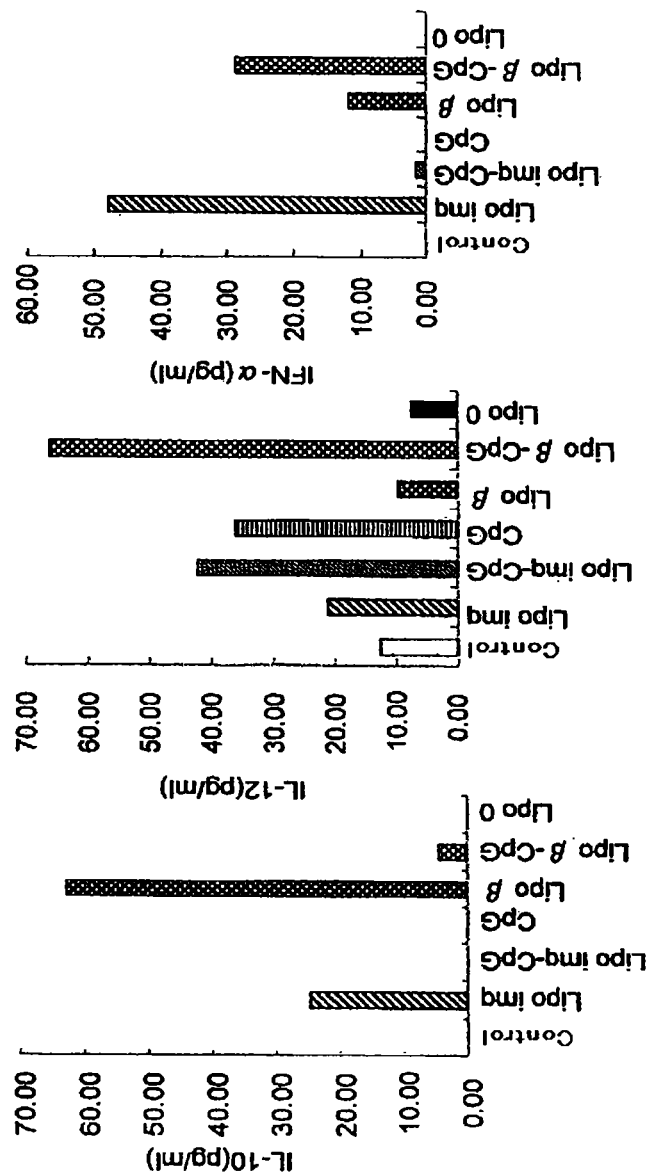
FIG. 1 shows results of in vitro cytokine production experiments in which a Lipo-β composition or other liposome compositions or saline was added to a culture system of $CD11c^+$ DC from spleen of BALB/c mice. A vertical axis shows concentrations of various cytokines in culture supernatants after the addition.

Herein, "regulatory cells" includes but is not limited to NKT cells (natural killer T cells), IL-10-producing Tr1 cells and dendritic cells (DC), and among them, the NKT cell is particularly preferable.

A "regulatory cell ligand" is not particularly limited as long as the ligand is bound to a cell surface receptor on the above regulatory cell to facilitate differentiation/proliferation or activation of the regulatory cell, and includes the followings. But, the regulatory cell ligand is not limited thereto.

(i) Galactosyl ceramides such as α-galactosyl ceramide and β-galactosyl ceramide substance which are the ligands of the NKT cells.

(ii) Vitamin D3, dexamethasone, TGF-β and IL-10 which serve for the differentiation/proliferation of regulatory dendritic cells (DC).

(iii) Substances which induce the expression of IL-10 or FoxP3 which serves for the differentiation/proliferation of regulatory T cells.

(iv) IGb3 (Isoglobo-glycosphingolipid) present in vivo.

A "regulatory cell-inducing agent" of the present invention refers to a medicament which induces the differentiation/proliferation or the activation of the regulatory cells. The facilitation of the differentiation/proliferation or the activation of the regulatory cells can be identified, for instance, as described in Examples, by using spleen CD11c$^+$ DC and measuring the proliferation of the NKT cells or the IL-10-producing Tr1 cells contained therein, or quantifying cytokines (IFN-γ, IL-10, IL-4) produced by NKT cells and the IL-10-producing Tr1 cells.

As a "liposome containing the regulatory cell ligand" of the present invention, those inducing the NKT cells and the IL-10 producing Tr1 cells which are the regulatory cells, further having an activity to suppress the activation of helper T cells and having an inhibitory action on the production of IgE antibody released from B cells are preferable. Specifically, those containing the "regulatory cell ligand" as the above in the liposome are preferable, and among them a composition including α-galactosyl ceramide or β-galactosyl ceramide in a lipid double membrane of the liposome is preferable. The "liposome containing the regulatory cell ligand" of the present invention may contain two or more "regulatory cell ligands".

The "liposome containing the regulatory cell ligand" of the present invention may further contain TLRs (Toll-like receptor) family ligands in addition to the regulatory cell ligand.

The addition of the TLRs family ligands can increase the production of cytokines which regulate the action of the "regulatory cells" and further enhances the effect. The TLRs family ligands include CpG oligonucleotide (CpGODN) and imiquimod (1-(2-methylproryl)-1H-imidazo[4,5-c]quinolin-4-amine).

The "liposome containing the regulatory cell ligand" may also contain one or more selected from the group consisting of allergens, autoantigens and derivatives thereof, which derivatives are antigens having one or more T cell epitopes.

The allergen is not particularly limited as long as it is a factor which the living body is exposed to, the living body ingests or is applied to the living body and can cause the allergy. Such an allergen includes pollens (e.g., Japanese cedar, Japanese cypress, ragweed, rice plant, white birch, cocksfoot, felon herb), foods (e.g., cow milk, buckwheat, egg, peanut, wheat, soy bean, fish, fruit, and processed products thereof), organisms other than human beings or things derived therefrom (e.g., mites, fungi, body hairs from animals and birds, bee toxin), medicaments (e.g., penicillin based antibiotics, sulfa drugs, barbituric acid derivatives), medical items (e.g., natural rubber gloves), livingwares (e.g., metals of accessories), and factors capable of causing the allergy included in other substances or compositions (latex). Specifically the allergen includes OVA (ovalbumin), ragweed antigen Amb a1 and cedar pollen antigens such as Cryj1 and Cryj2.

The drug of the present invention is useful as the therapeutic agent specific for the allergic disease caused by an allergen or derivative thereof when the drug contains the allergen or derivative thereof. The present inventors have found that since the liposome containing the regulatory cell ligand and an allergen specifically inhibits the production of IgE caused by the allergen, the allergic disease caused by the allergen can be treated with such a liposome. The allergic diseases capable of being specifically treated with the drug of the present invention include atopic bronchial asthma, atopic dermatitis, allergic rhinitis (e.g., pollen disease), allergic conjunctivitis, food allergy and medicament allergy.

An autoantigen is not particularly limited as long as it is the antigen which can be targeted by immune cells in autoimmune diseases. The autoantigen includes, for example, collagen, nucleic acids (rheumatoid arthritis, systemic lupus erythematosus), myelin basic protein (MBP) (multiple sclerosis), thyroglobulin (thyroid autoimmune disease) and graft allogenic antigen (graft versus host disease).

The drug of the present invention is useful as the therapeutic agent for the autoimmune disease when the drug contains the liposome containing one or more selected from the group consisting of autoantigens and derivatives thereof, which derivatives are antigens having one or more T cell epitopes. The present inventors have found that the liposome containing the regulatory cell ligand and an allergen can specifically treat the allergic disease caused by the allergen, and thus have conceived that the autoimmune disease caused by an autoantigen can be similarly treated specifically by utilizing a medicament delivery vehicle containing the autoantigen in place of the allergen. Such an autoimmune disease includes, for example, those described above.

The present invention provides the liposome in which the regulatory cell ligand as the above, preferably a lipid-soluble compound such as galactosyl ceramide has been incorporated as a water soluble macromolecular substance. Herein, one having a vesicular structure where a micelle (water soluble particle obtained by aggregating amphipathic molecules including hydrophilic region and a hydrophobic region) has been closed is referred to as the liposome. A liposome component may be any ones as long as it is the amphipathic molecule which can form the micelle by known methods, and preferably includes lipids. The lipid in the present invention includes phospholipids such as dipalmitoylphosphatidylcholine (DPPC), dioleylphosphatidylcholine (DOPC) and dioleylphosphatidyl ethanolamine (DOPE), sphingoglycolipid and glyceroglycolipid. These are used for making the liposome, alone or in combination of two or more or in combination with a lipid derivative where a non-polar substance such as cholesterol or a water soluble polymer such as polyethylene glycol has been bound to the lipid.

The liposome can be prepared in accordance with publicly known methods. For example, the methods described in Liposome Technology, vol. 1, $2^{nd}$ edition (by Gregory Gregoriadis (CRC Press, Boca Raton, Ann Arbor, London, Tokyo), Chapter 4, pp 67-80, Chapter 10, pp 167-184 and Chapter 17, pp 261-276 (1993)) can be used. More specifically, the methods include, but are not limited to, a sonication method, an ethanol injection method, a French press method, an ether injection method, a cholic acid method, a calcium fusion method, a lyophilization method and a reverse phase evaporation method. A size of the liposome of the present invention is not particularly limited, and typically is preferably 100 to 200 nm and more preferably 100 to 150 nm in average. The structure of the liposome is not particularly limited, and may be any liposome such as unilamella and multilamella. As a solution encapsulated inside the liposome, it is possible to use buffer and saline and others in addition to water. It is also possible to add a water soluble organic solvent (e.g., glycerine) in an appropriate amount thereto and use it.

The liposome used for the drug of the present invention may be those obtained by modifying the liposome surface for targeting the "liposome containing the regulatory cell ligand" to a target site. The target site includes, for example, liver, spleen, lymph node, bone marrow, lung, eye, skin and nose.

The substance which modifies the liposome surface includes low molecular compounds, high molecular compounds, nucleic acids, peptides, proteins and sugar chains. The high molecular compound includes polyethylene glycol (see U.S. Pat. No. 2,948,246). The nucleic acid includes, for example, single strand RNA and single strand DNA which recognize TLR-7 or TLR-9 of the Toll-like receptor in the target cell, and derivatives of these nucleic acids. The protein includes, for example, antibodies and receptors which recognize the molecules expressed specifically on the surface of the target cells such as dendritic cells (DC) which are antigen presenting cells or precursor cells thereof. The modification with the sugar chain includes the modification with mannose bound lipid which can be bound to a mannose receptor expressed on the surface of DC (e.g., see Copland, M. J., et al., (2003) Liposome delivery of antigen to human dendritic cells, Vaccine, 21:883-890).

Inclusion of the ligand into the liposome can be performed by ordinary methods. For example, as shown in Examples, the liposome containing the regulatory cell ligand can be obtained by separately dissolving the liposome component and the ligand in the organic solvent, mixing these and adding water. But the method for producing the liposome containing the regulatory cell ligand is not limited to the above.

The "liposome containing the regulatory cell ligand" can be used as the active ingredient of the drug.

That is, the drug of the present invention is effective as the preventive agent or the therapeutic agent for the allergic diseases caused by IgE antibody because the "liposome containing the regulatory cell ligand" induces the NKT cells or the IL-10-producing Tr1 cells which are the regulatory cells, has the activity to suppress the activation of the helper T cells and has the inhibitory action on the production of the IgE antibody released from B cells. The IgE antibody is particularly deeply associated with the allergic diseases, and thus by suppressing the production (secretion) thereof, it is possible to obtain the preventive or therapeutic effect on the type I allergic diseases. The allergic diseases associated with the IgE antibody include atopic bronchial asthma, atopic dermatitis and nasal allergy such as allergic rhinitis and pollinosis. In the present invention, the prevention of the allergic disease encompasses not only making mammalian animals including human beings who have not had the allergic disease free from the disease but also making the patients (mammalian animals including human beings) with allergic disease who have not had the symptom temporarily free from the symptom.

The drug of the present invention is also effective as the preventive agent or the therapeutic agent for the disease such as fulminant hepatitis because the "liposome containing the regulatory cell ligand" has the action to suppress the activation of the T cells.

The drug containing the liposome containing α-galactosyl ceramide as the active ingredient is effective as the drug having an immunosuppressive ability because the liposome containing α-galactosyl ceramide has the effect to selectively augment the immunosuppressive function of the NKT cells. Specifically, the drug is effective as the drug for autoimmune diseases such as rheumatoid, multiple sclerosis, systemic lupus erythematosus and collagen disease and the drug for rejection upon transplantation such as GVHD.

α-Galactosyl ceramide is not particularly limited as long as it is bound to the surface receptor of the NKT cell to selectively augment the immunosuppressive function of the NKT cell, but is preferably one bound to the receptor composed of Vα24JαQ in human or Vα14Jα281 in mouse. The molecular weight thereof is preferably 400 to 2,000.

Meanwhile, the molecular weight of β-galactosyl ceramide used for the present invention is preferably 400 to 2,000.

As another embodiment of the present invention, the drug comprising the liposome containing imiquimod, as the active ingredient is provided. By containing imiquimod in the liposome, the production amounts of IL-10 and IFNα are enhanced thereby activating the NKT cells compared with the case of using imiquimod alone. Therefore, the drug comprising the liposome containing imiquimod as the active ingredient is useful for the prevention or the treatment of the allergic diseases as described above.

For an administration route of the drug of the present invention, the drug can be administered both orally or parenterally, and the route is optionally selected by a physician. The "liposome containing the regulatory cell ligand" as the active ingredient can be administered alone or in combination with a carrier usually used.

When the drug of the present invention is orally administered, a form of the drug includes solid formulations such as tablets, coated tablets, powdered agents, granules, capsules and pills, liquid formulations such as liquid agents (e.g., eye drops, nose drops), suspension, emulsion and syrup, inhales such as aerosol agents, atomizers and nebulizers, and liposome inclusion agents.

When the drug of the present invention is parenterally administered, the form of the drug includes injectable agents (liquid agents, suspensions) used for intravenous injection, subcutaneous injection, intraperitoneal injection, intramuscular injection and intraperitoneal injection, liquid agents, suspensions, emulsions and dripping agents.

When the drug of the present invention is the liquid formulation, the drug may be stored in a frozen state or lyophilized by removing the water. Injectable distilled water is added to the lyophilized formulation to re-dissolve the formulation before use.

As pharmaceutically acceptable carriers utilized for the drug of the present invention, it is possible to exemplify binders, disintegrants, surfactants, absorption accelerators, moisture retention agents, absorbers, lubricants, fillers, extenders, moisture imparting agents, preservatives, stabilizers, emulsifiers, solubilizing agents, salts which control osmotic pressure, diluting agents such as buffers and excipients usually used depending on the use form of the formulation. These are optionally selected and used depending on the unit dosage of the resulting formulation.

Additionally, coloring agents, preserving agents, perfumes, flavors and sweeteners, and other pharmaceutical articles can be contained in the drug of the present invention as needed to prepare as the agent.

An effective amount of the "liposome containing the regulatory cell ligand" can be easily determined by those skilled in the art with reference to the conventional art, and is, for example, about 0.1 to 100 mg per 1 kg of body weight and preferably about 1 to 10 mg, and this can be administered by dividing into 1 to 3 times daily. It is preferable to optionally regulate the dosage depending on the form of each formulation, a gender, an age and a disease condition of the patient.

EXAMPLES

The present invention will be described with reference to the following Examples, but the present invention is not limited to these Examples, and it goes without saying that usual changes in the art of the present invention can be made.

Example 1

Preparation of Ligand-Containing Liposome and Measurement of Activity

1. Preparation of β-Galactosyl Ceramide-Containing Liposome (Lipo-β)

L-α-Phosphatidylethanolamine, dioleoyl (DOPE; Wako Pure Chemical #166-16183, 0.77 mg), 0.83 mg of cholesteryl 313-N-(dimethylaminoethyl)carbonate hydrochloride (DC-Chol; SIGMA-Aldrich) and 0.029 mg of 1,2-distearoyl-sn-glycero-3-phosphoethanolamine-N-[methoxy(polyethylene glycol)-2000] (AVANTI POLAR-LIPIDS, INC. #i88653) were dissolved in 250 μL of chloroform/methanol (1:1) solvent. β-Galactosyl ceramide (ceramide β-D-galactoside; Sigma-Aldrich #C4905, 0.16 mg) was separately dissolved in 250 μL of chloroform/methanol (1:1) solvent. Both were mixed and evaporated using an evaporator, and subsequently dried overnight in a desiccator under vacuum. Then, 800 μL of water was added, the mixture was treated with a sonicator for one minute, then particle sizes were selected by filtration with pressure using an extruder (AVESTIN; LiposoFast-Basic), and the particles were sterilized with a membrane having a pore size of 0.22 μm. This liposome composition (Lipo-β) was adjusted to a final concentration of 200 μL/mL. By the same method, a liposome composition containing no β-galactosyl ceramide (Lipo-0) was prepared. An eluted product collected through a salting out column NAP-10 after mixing oligonucleotide CpGODN (1668) (supplied from SIGMA GENOSIS) with Lipo-β at a weight ratio of 5:1 was rendered Lipo-β-CpG.

2. Preparation of Imiquimod-Containing Liposome

L-α-Phosphatidylethanolamine, dioleoyl (DOPE; Wako Pure Chemical #166-16183, 0.77 mg), 0.83 mg of cholesteryl 3β-N-(dimethylaminoethyl)carbonate hydrochloride (DC-Chol; SIGMA-Aldrich) and 0.029 mg of 1,2-Distearoyl-sn-Glycero-3-Phosphoethanolamine-N-[Methoxy(polyethylene glycol)-2000] (AVANTI POLAR-LIPIDS, INC. #188653) were dissolved in 250 μL of chloroform/methanol (1:1) solvent. Imiquimod (Sequoia Research Products Ltd; SRP0058i, 0.16 mg) was separately dissolved in 250 μL of chloroform/methanol (1:1) solvent. Both were mixed and evaporated using an evaporator, and subsequently dried overnight in a desiccator under vacuum. Then, 800 μL of water was added, the mixture was treated with the sonicator for one minute, then particle sizes were selected by filtration with pressure using the extruder (AVESTIN; LiposoFast-Basic), and the particles were sterilized with the membrane having a pore size of 0.22 μm. This liposome composition (Lipo-Imq) was adjusted to a final concentration of 200 μL/mL. By the same method as in the above composition, a liposome composition (Lipo-Imq-βGC) containing ceramide β-D-galactoside (Sigma-Aldrich #C4905) was prepared. An eluted product collected through the salting out column NAP-10 after mixing oligonucleotide CpGODN (1668) (supplied from SIGMA GENOSIS) with Lipo-Imq at a weight ratio of 5:1 was rendered Lipo-Imq-CpG.

3. Measurement of In Vitro Activity of Ligand-Containing Liposome for Dendritic Cells (DC)

Figure 2:
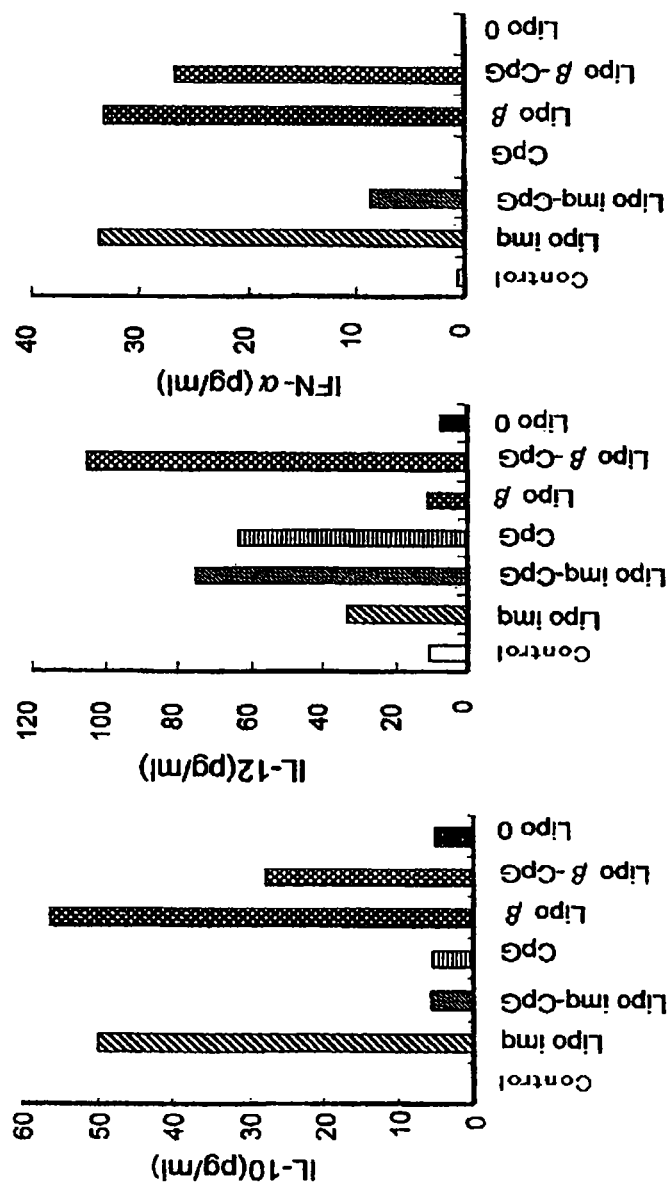
FIG. 2 shows results of in vitro cytokine production experiments in which the Lipo-β composition or the other liposome compositions or saline was added to the culture system of $CD11c^+$ DC from spleen of C57BL/6 mice. The vertical axis shows the concentrations of various cytokines in the culture supernatants after the addition.
Figure 3:
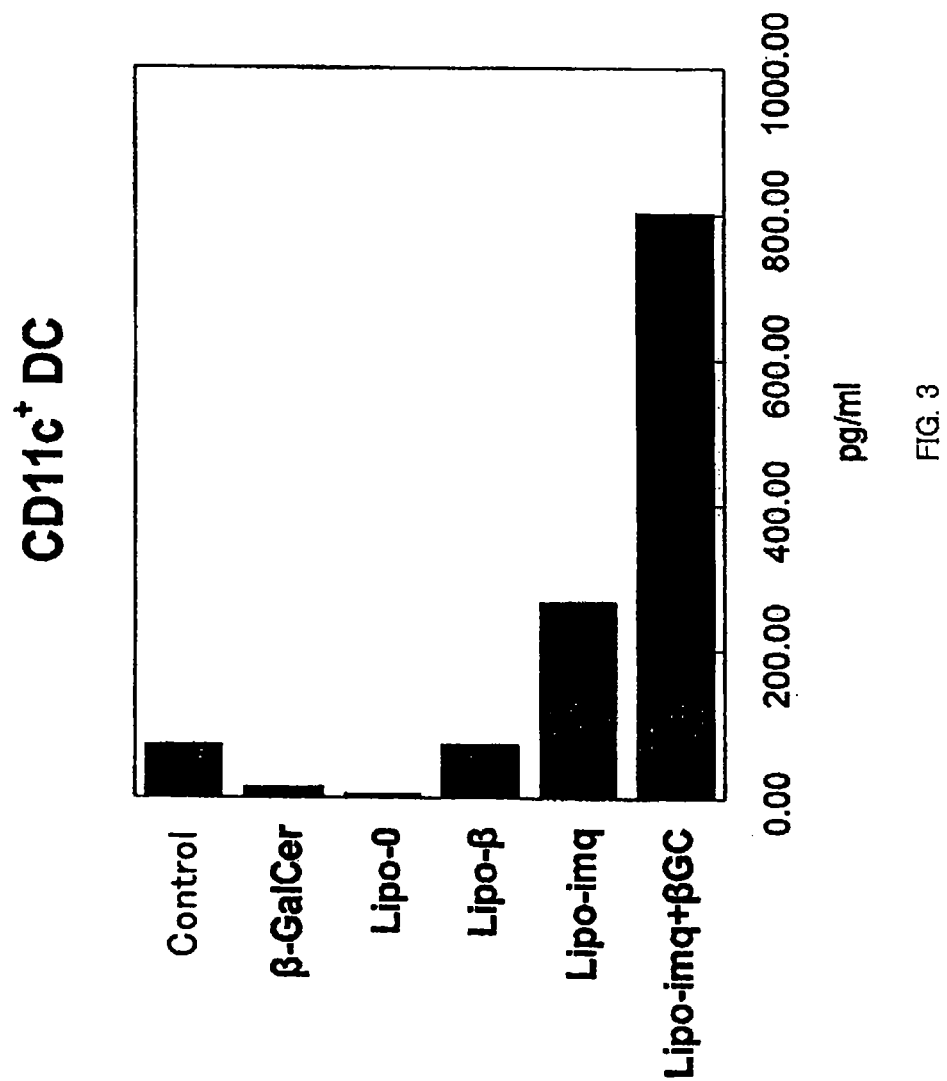
FIG. 3 shows results of in vitro cytokine production experiments in which the Lipo-β composition or the other liposome compositions or saline was added to the culture system of $CD11c^+$ DC from spleen of BALB/c mice. The vertical axis shows the concentrations of IL-10 in the culture supernatants after the addition.

Collagenase D (1 mg/mL, Roche) was injected into spleen from BALB/c or C57BL/6 mouse, which was then incubated in a $CO_2$ incubator for 45 minutes. Subsequently, cells were collected from the spleen, suspended in 3 mL of HistoDenz (14.1%, SIGMA), and then X-VIVO 15 (Takara Bio) containing 50 μM 2-mercaptoethanol (2ME) was overlaid thereon. After centrifuging at 1,500 rpm for 5 minutes, the cells in an intermediate layer were collected and incubated in X-VIVO 15 medium containing 50 μM 2ME, 0.5% fetal calf serum and 20 ng/mL rmGM-CSF (Pharmingen) in the $CO_2$ incubator for one and a half hours. After pipetting gently, the suspended cells were removed, the X-VIVO 15 medium containing 50 μM 2ME, 0.5% fetal calf serum and 20 ng/mL rmGM-CSF (Pharmingen) was added, and the cells were incubated in the $CO_2$ incubator for 18 hours. The suspended cells were collected, and the cells bound to anti-CD11c antibody-magnetic microbeads (Miltenyi) were collected to render spleen $CD11c^+$ DC. The $CD11c^+$ DC at $1\times10^4$ cells were suspended in 200 μL of RPMI medium containing 10% fetal calf serum in a 96-well round bottom microtiter plate, the liposome composition at a final concentration of 1 μg/mL was added thereto, and the plate was incubated in the incubator containing 5% $CO^2$ at 37° C. After 48 hours, culture supernatants were collected, and levels of IFN-α, IL-10 and IL-12 were measured by ELISA (FIGS. 1 and 2). The levels of IL-10 and IFN-α were high whereas the levels of IL-12 were low in Lipo-β and Lipo-Imq groups. Conversely, in Lipo-β-CpG and Lipo-Imq-CpG groups, the levels of IL-10 and IFNα were low whereas the levels of IL-12 were high. Meanwhile, in the non-addition group (control), Lipo-0 and the β-galactosyl ceramide solution (β-GalCer) groups, the production of all cytokines was not detected or was very low. In the same evaluation method, the production levels of IL-10 in $CD11c^+$ DC by Lipo-Imq-βGC were measured. As a result, it was found that Lipo-Imq-βGC induced IL-10 production at much higher levels than Lipo-β alone or Lipo-Imq alone (FIG. 3).

Example 2

Inhibitory Effect of Lipo-β on In Vivo Production of IgE Antibody

Figure 4:
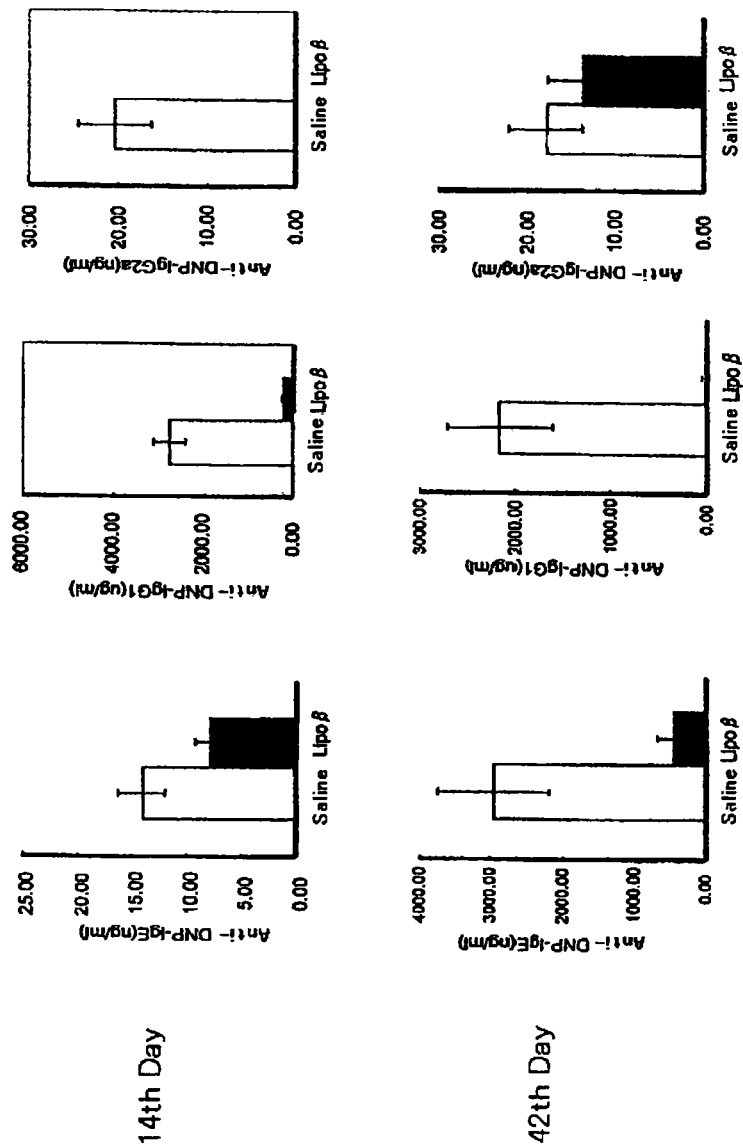
FIG. 4 shows the results of measuring the production of DNP-OVA specific antibody in plasma by ELISA. BDF1 mice were administered with Lipo-β or saline, then immunized with DNP-OVA and alum followed by being boosted with DNP-OVA alone. ELISA was performed after the primary immunization and after the boosting.

Lipo-β (2 μg/mouse) was intraperitoneally injected in BDF1 mice (5 mice/group), after 7 days (day 0), which were primarily immunized with 0.1 μg of DNP-OVA (Cosmobio) and 10 mg of alum. On the 14th day after the primary immunization, blood was collected from orbital venous plexus, and antibody titers of ant-DNP-IgG1, anti-DNP-IgE and anti-DNP-IgG2a in plasma were measured by ELISA (14th day in FIG. 4). The mice were boosted with DNP-OVA alone on the 35th day after the primary immunization, and 7 days thereafter, the antibody titers of anti-DNP-IgG1 and anti-DNP-IgE in the plasma from the blood collected from the orbital venous plexus were measured by ELISA (42nd day in FIG. 4). In the Lipo-β group, on the day 14, the production of IgG antibody and IgE antibody tended to be already inhibited, and on the day 42, the increase of IgG antibody and IgE antibody was completely inhibited after the boost immunization.

Example 3

Induction of Regulatory T Cells by Dendritic Cells (DC) Derived from Mice Administered with Lipo-β

1. Evaluation of in vitro activation ability of T cells

Figure 5:
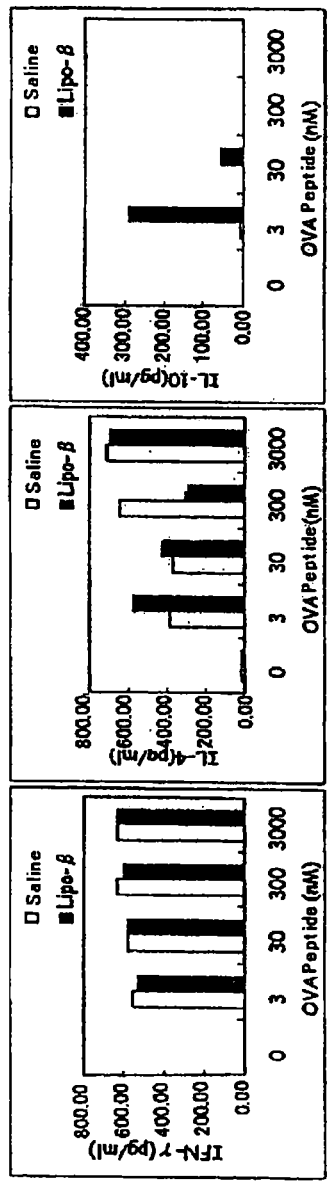
FIG. 5 shows the results of measuring the concentrations of cytokines in culture supernatants after culturing $CD11c^+$ cells obtained from spleen of BALB/c mice 7 days after Lipo-β or saline (negative control) was administered and $CD4^+$ T cells derived from DO11.10 mice (transgenic mice transfected with OVA specific TCRαβ) in the presence of OVA peptide for 4 days.

Lipo-β or saline (2 μL/mouse) was intraperitoneally administered to BALB/c mice, and after 7 days, the spleen was removed. Collagenase D (1 mg/mL, Roche) was injected into the spleen, which was then incubated in the $CO_2$ incubator for 45 minutes. Subsequently, cells were collected from the spleen, suspended in 3 mL of HistoDenz (14.1%, SIGMA), and then X-VIVO 15 containing 50 μM 2-mercaptoethanol (2ME) was overlaid thereon. After centrifuging at 1,500 rpm for 5 minutes, the cells in the intermediate layer were collected and incubated in the X-VIVO 15 medium containing 50 μM 2ME, 0.5% fetal calf serum and 20 ng/mL rmGM-CSF (PharMingen) in the $CO_2$ incubator for one and a half hours. After pipetting gently, the suspended cells were removed, the X-VIVO 15 medium containing 50 μM 2ME, 0.5% fetal calf serum and 20 ng/mL rmGM-CSF (PharMingen) was added, and the cells were incubated in the $CO_2$ incubator for 18 hours. The suspended cells were collected, and the cells bound to anti-CD11c antibody-magnetic microbeads (Miltenyi) were collected to render spleen $CD11c^+$ DC. $CD4^+$ T cells were collected from OVA specific TCRαβ transgenic mouse DO11.10 (given by Dr. Toshinori Nakayama, Graduate School of Medicine, Chiba University; Science, 1990, vol. 250, p 1720) using antibody-magnetic microbeads (Miltenyi). Subsequently, $CD11c^+$ DC at $2\times10^4$ cells and $CD4^+$ T cells at $1\times10^5$ cells were cultured in the presence of the OVA peptide in the $CO_2$ incubator for 4 days, then the culture supernatant was collected, and the levels of IFNγ, IL-4 and IL-10 were measured by ELISA (FIG. 5). As a result, when DC from the spleen of the mouse administered with Lipo-β were used and when DC from the spleen of the mouse administered with saline (normal) were used, no difference was observed in the levels of IL-4 and IFN-γ production. However, the production of IL-10 was observed only at OVA peptide concentrations of 3 nM and 30 nM when DC from the spleen of the mouse administered with Lipo-β were used. Simultaneously, the proliferation of the regulatory cells was also identified.

Figure 6:
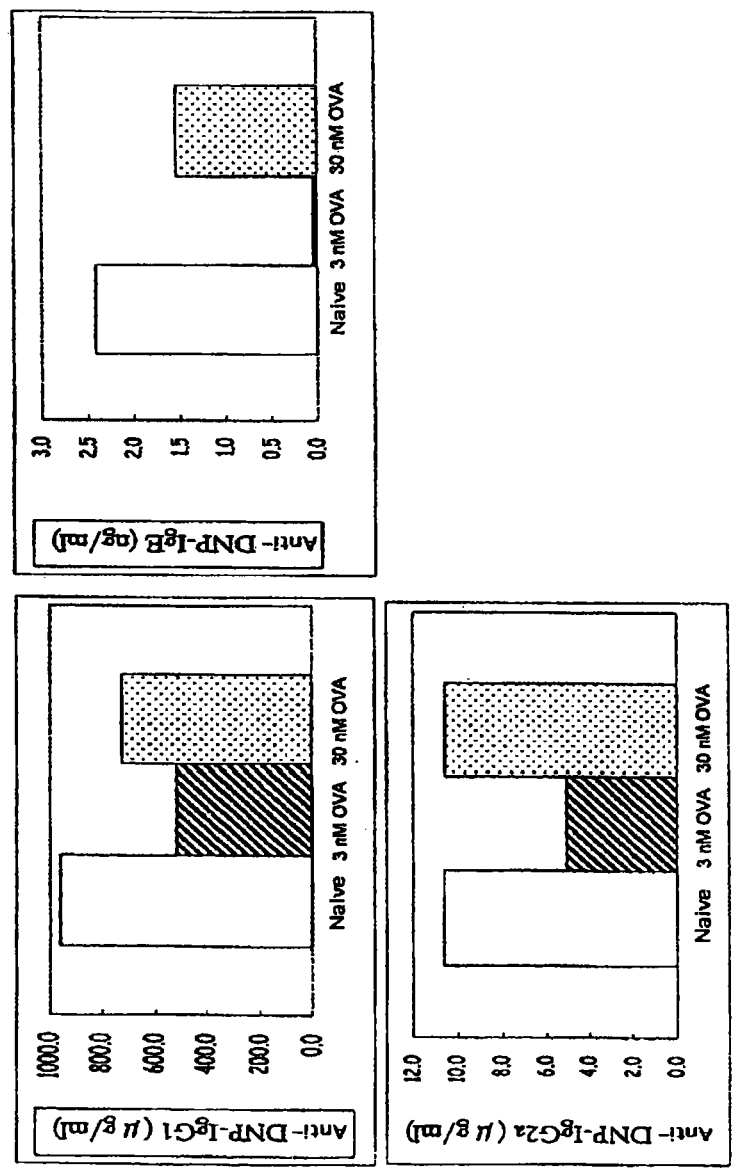
FIG. 6 shows the results of measuring antibody titers in blood on the 14th days after immunizing with DNP-OVA and alum after the cells which proliferated in the experiments in FIG. 5 were adoptively transferred in BALB/c mice.

2. Evaluation of Inhibitory Effect on In Vivo IgE Antibody Production by Adoptive Transfer Method DO11.10-CD4$^+$ T cells which had proliferated at OVA peptide concentrations of 3 nM or 30 nM and DC from the spleen of the mouse administered with Lipo-β in the above 1. in vitro experiment were collected, and 1×10$^6$ thereof were intraperitoneally transferred into BALB/c mice (3 mice/group). After one hour, the mice were primarily immunized with DNP-OVA (10 μg) and alum (10 mg), and on the 14th day, the blood was collected from the orbital venous plexus. The antibody titers of anti-DNP-IgG1, anti-DNP-IgE and anti-DNP-IgG2a in the plasma were measured by ELISA (FIG. 6). As a result, the production of IgE antibody was completely inhibited in the mice in which DO11.10-CD4$^+$ T cells grown by the stimulation of OVA peptide at 3 nM had been adoptively transferred. Meanwhile, the inhibitory effect on the IgE antibody production was low in the mice in which DO11.10-CD4$^+$ T cells grown by the stimulation of OVA peptide at 30 nM had been adoptively transferred. The inhibition of IgG1 and IgG2a antibody production was not remarkable in both groups.

Example 4

Preparation of Ligand-Containing Liposome and Measurement of Activity

1. Preparation of α-Galactosyl Ceramide-Containing Liposome

L-α-Phosphatidylethanolamine, dioleoyl (DOPE; Wako Pure Chemical #166-16183, 0.77 mg) and 0.83 mg of cholesteryl 3β-N-(dimethylaminoethyl)carbonate hydrochloride (DC-Chol; Sigma-Aldrich #C2832) were dissolved in 250 μL of chloroform/methanol (1:1) solvent. α-Galactosyl ceramide (0.16 mg, supplied from RIKEN Research Center for Allergy and Immunology; KRN7000, see International Publication Pamphlet WO98/44928) was separately dissolved in 250 μL of chloroform/methanol (1:1) solvent. Both were mixed and evaporated using the evaporator, and subsequently dried overnight in the desiccator under vacuum. Then, 800 μL of water was added, the mixture was treated with the ultrasonic pulverizer for one minute, and passed through a membrane having a pore size of 0.22 μm for sterilization. This liposome composition (Lipo-αGC) was adjusted to a final concentration of 200 μL/mL. By the same method, a liposome composition containing no α-galactosyl ceramide (Lipo-(−)) for the control was prepared.

2. Measurement of Cytokine Production by Lipo-αGC

Figure 7:
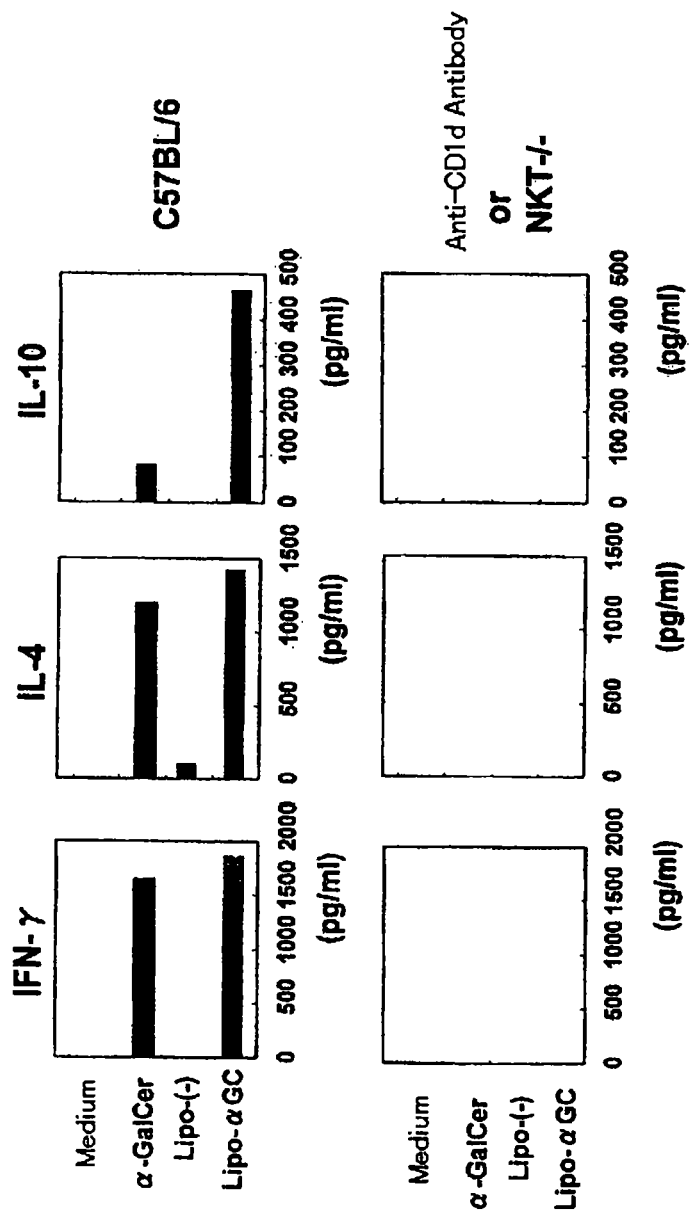
FIG. 7 shows the results of measuring the in vitro production of cytokines. Medium, an aqueous solution of α-galactosyl ceramide (α-GalCer), a liposome composition as the control (Lipo-(−)) or an α-galactosyl ceramide-containing liposome (Lipo-αGC) was added to the cultures of whole spleen cells (upper panels) and the spleen cells to which anti-CD1d neutralization antibody had been added or in which NKT cells had been deleted (lower panels) in C57BL/6 mice. The horizontal axis represents the concentration of each cytokine in the culture supernatant 2 days after the addition.

Spleen whole cells at 2×10$^5$ from C57BL/6 mouse were suspended in 200 μL of 10% fetal calf serum (FCS)-containing RPMI medium to which 100 ng/mL Lipo-(−), Lipo-αGC or α-galactosyl ceramide aqueous solution (α-GalCer) had been added, then the cell suspension was added to a 96-well U bottom culture plate, and cultured in the incubator containing 5% $CO_2$ at 37° C. for 2 days. The levels of IFN-γ, IL-4 and IL-10 produced in the culture supernatant were measured by ELISA (FIG. 7 upper panels). The levels of IFN-γ and IL-4 were equivalent in Lipo-αGC group and αGalCer group, but the level of IL-10 in the Lipo-α group was 5 times higher than that in the α-GalCer group. When the same experiments were performed in the presence of anti-CD1d neutralization antibody (1B1, BD Bioscience PharMingen) at a final concentration of 10 μg/mL or using spleen whole cells from Vα14-NKT cell-deficient mouse (C57BL/6 background), IFN-γ, IL-4 and IL-10 in the culture supernatant were not detected (FIG. 7, lower panels).

3. Evaluation of Vα14-NKT Cell Proliferation Ability by Lipo-αGC

Figure 8:
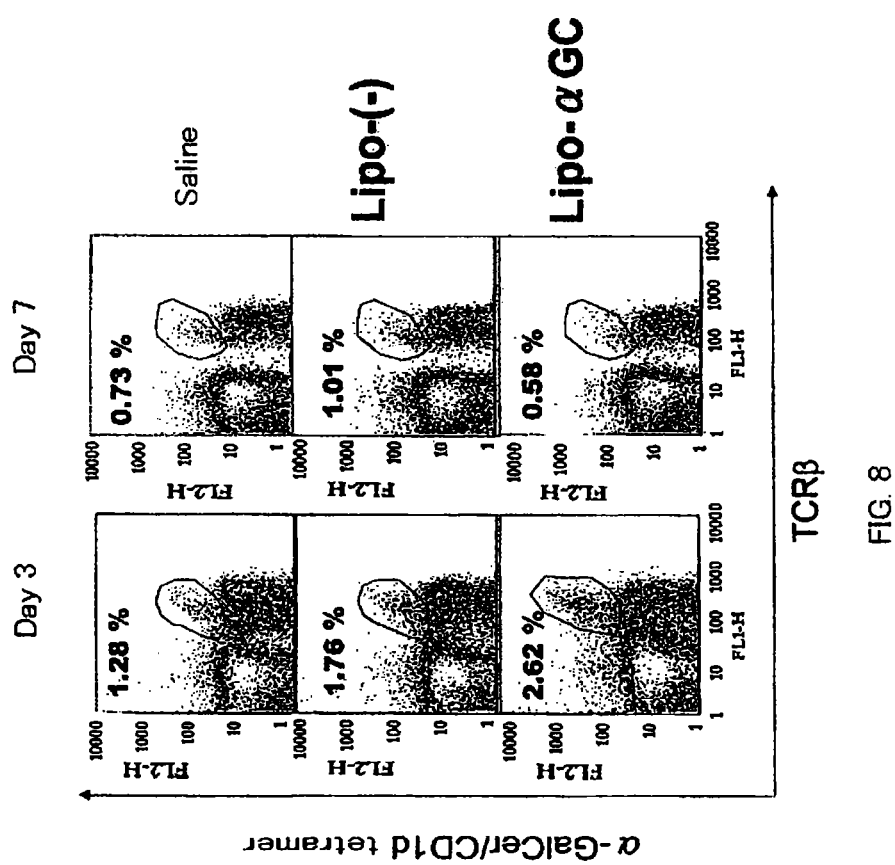
FIG. 8 shows the results of analyzing the numbers of Vα14-NKT cells in the spleen by flow cytometry 3 days or 7 days after saline, Lipo-(−) or Lipo-αGC was administered to C57BL/6 mice. The horizontal axis and the vertical axis represent fluorescence intensity of FITC-labeled anti-TCRβ antibody and PE-labeled CD1d tetramer+ α-GalCer, respectively.

Lipo-αGC (2 μg/mouse), or Lipo-(−) or saline as the control was intraperitoneally administered to C57BL/6 mice. On the 3rd day (day 3) and the 7th day (day 7), the spleen cells were stained with αGalCer/CD1d tetramer and anti-TCRβ antibody, and the number of double positive cells (Vα14-NKT cells) was analyzed by flow cytometry. As a result, it was identified that the number of the Vα14-NKT cells in the spleen of the mouse 3 days after the administration of Lipo-α was increased 2 times or more compared with that from the spleen administered with saline, but on day 7, the number was reversely reduced compared with that from the control mice (FIG. 8).

Example 5

Inhibitory Effect of Lipo-αGC on In Vivo Antibody Production

Figure 9:
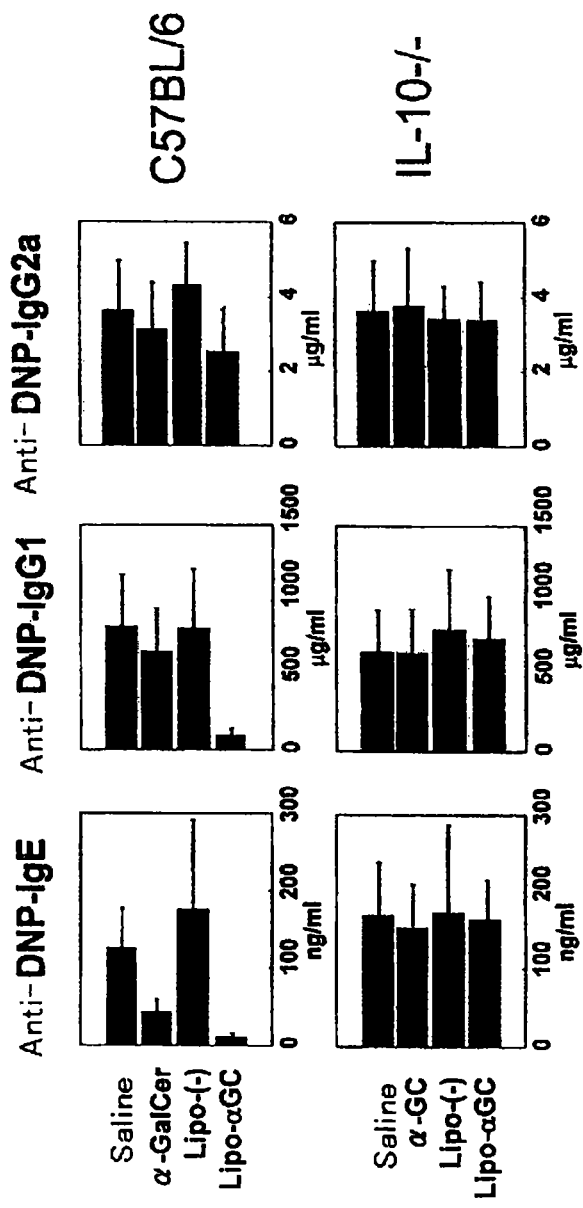
FIG. 9 shows antibody titers of anti-NP-IgE, anti-NP-IgG1 and anti-NP-IgG2a in blood. Saline, α-GalCer, Lipo-(−) or Lipo-αGC was administered to C57BL/6 mice (upper panels) or IL-10 gene-deficient mice (lower panels), after 3 days, which were immunized with DNP-OVA and alum, and after 14 days, the titers were measured.

1. Activity Evaluation in In Vivo Antibody Production System Using C57BL/6 and IL-10-Deficient Mice Saline, α-GalCer, Lipo-(−) or Lipo-αGC (2 μg/mouse) was intraperitoneally administered in C57BL/6 mice (5 mice/group), after 3 days, which were primarily immunized with DNP-OVA and alum. On the 14th day after the primary immunization, the blood was collected from the orbital venous plexus, and antibody titers of ant-DNP-IgG1, anti-DNP-IgE and anti-DNP-IgG2a in the plasma were measured by ELISA. As a result, the inhibitory effect on the antibody production in the Lipo-αGC group tended to be higher than in the α-GalCer group for all isotypes examined (FIG. 9 upper panels). The same experiment was performed using the IL-10-deficient mice with C57BL/6 background. As a result, no inhibitory effect on the antibody production was observed (FIG. 9 lower panels).

2. Activity Evaluation in In Vivo Antibody Production System Using BDF1 Mice

Figure 10:
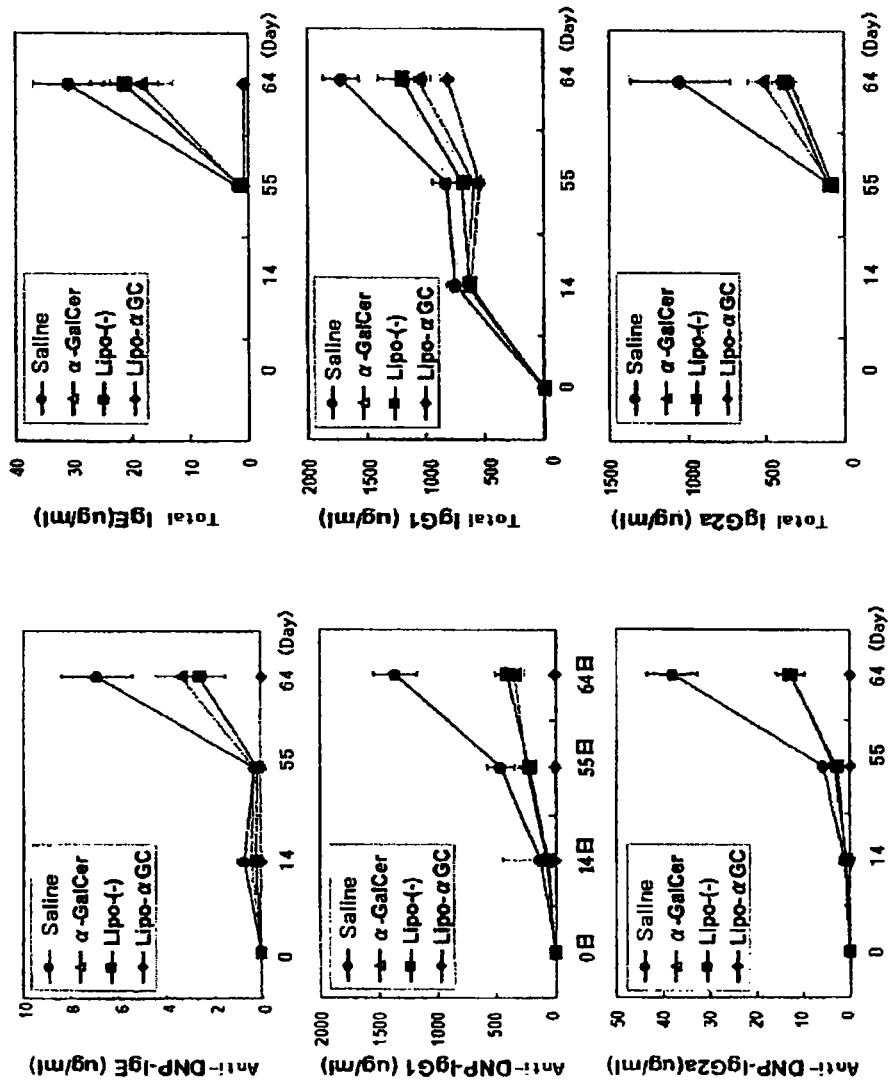
FIG. 10 shows antibody titers of anti-DNP-IgE, anti-DNP-IgG1, anti-DNP-IgG2a, and levels of total IgE, total IgG1 and total IgG2a. Saline, α-GalCer, Lipo-(−) or Lipo-αGC was administered to BDF1 mice, after 3 days (day 0), which were immunized with DNP-OVA and alum, and boosted with DNP-OVA alone on day 55. The titers were measured on days 0, 14, 55 and 64.

Saline, α-GalCer, Lipo-(−) or Lipo-αGC (2 μg/mouse) was intraperitoneally administered in BDF1 mice (C57BL/6× DBA/2F1) (5 mice/group), after 3 days (day 0), which were primarily immunized with DNP-OVA and alum, and further the mice was boosted with DNP-OVA alone on the 55th day (day 55) after the primary immunization. On days 0, 14, 55 and 64, the blood was collected from the orbital venous plexus, and antibody titers of ant-DNP-IgE, anti-DNP-IgG1, anti-DNP-IgG2a, and the levels of total IgE, total IgG1 and total IgG2a in the plasma were measured by ELISA. As a result, it was identified that the increase of antibody titers of all isotype anti-DNP and the production of total IgE were nearly completely inhibited in the Lipo-αGC group (FIG. 10). Meanwhile, the changes of total IgG1 and total IgG2a were nearly equivalent in the Lipo-αGC group and the α-GalCer group or Lipo-(−) group (FIG. 10).

3. Evaluation of T Cell Activation Ability Using BDF1 Mice

Figure 11:
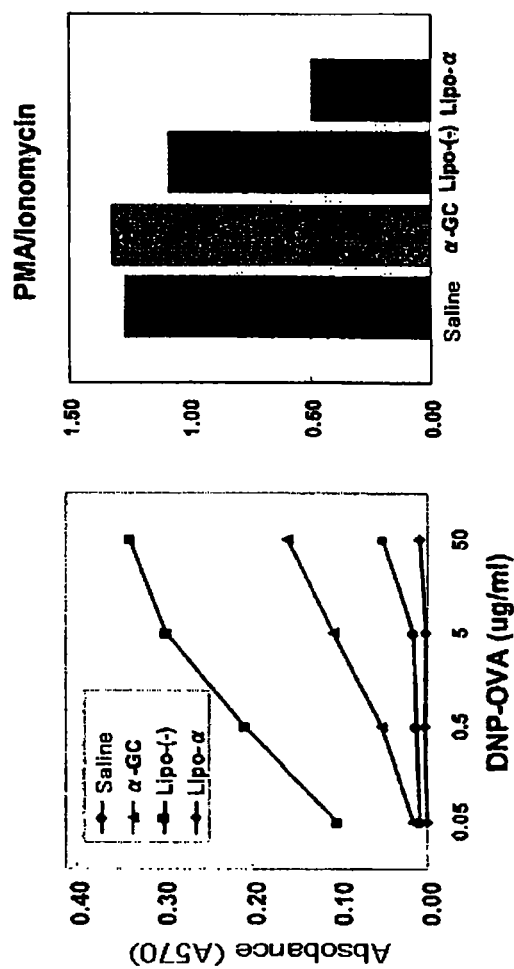
FIG. 11 shows the results of measuring cell proliferation ability by MTT method. Saline, α-GalCer, Lipo-(−) or Lipo-αGC was administered to BDF1 mice, after 3 days, which were immunized with DNP-OVA and alum. After 7 days, spleen CD4$^+$ T cells and radiation-irradiated whole spleen cells from intact BDF1 mice were stimulated with NDP-OVA or PMA/ionomycin. After 48 hours, the cell proliferation ability was measured. In the left figure, the horizontal axis and the vertical axis represent the concentration of DNP-OVA and absorbance at a wavelength of 570 nm, respectively.

Saline, α-GalCer, Lipo-(−) or Lipo-αGC (2 μg/mouse) was intraperitoneally administered in BDF1 mice, after 3 days, which were primarily immunized with DNP-OVA and alum. After 7 days, the spleen was removed, and CD4$^+$ T cells were prepared using magnetic microbeads (Miltenyi). Subsequently, antigen presenting cells were prepared by irradiating spleen whole cells from the normal BDF1 mouse with radiation of 20 Gy. The CD4$^+$ T cells at 2×10$^5$ and the antigen presenting cells at 2×10$^5$ pulsed with DNP-OVA suspended in 200 μL of the medium were placed in one well of the 96-well U bottom culture plate, and cultured in the incubator containing 5% $CO_2$ at 37° C. After 48 hours, cell proliferation was assayed by MTT method (Promega #G4000). As a results, the CD4$^+$ T cells derived from the spleen of the mouse administered with Lipo-αGC did not proliferate in response to DNP- OVA at all concentrations examined, while other CD4+ T cells highly proliferated in order of α-GalCer, saline and Lipo-(−) (FIG. 11 left panel). On the other hand, when the CD4+ T cells at 2×10^5 were stimulated antigen-non-specifically with 50 ng/mL of phorbol 12-miristate 13-acetate (PMA; Sigma-Aldrich #P-1585) and 500 nM ionomycin (Sigma-Aldrich, #I-0634) in the $CO_2$ incubator containing 5% $CO_2$ at 37° C. for 48 hours, the CD4+ T cells derived from the mouse administered with Lipo-αGC exhibited lower but significant proliferative response compared with other CD4+ T cells (FIG. 11, right panel).

Figure 12:
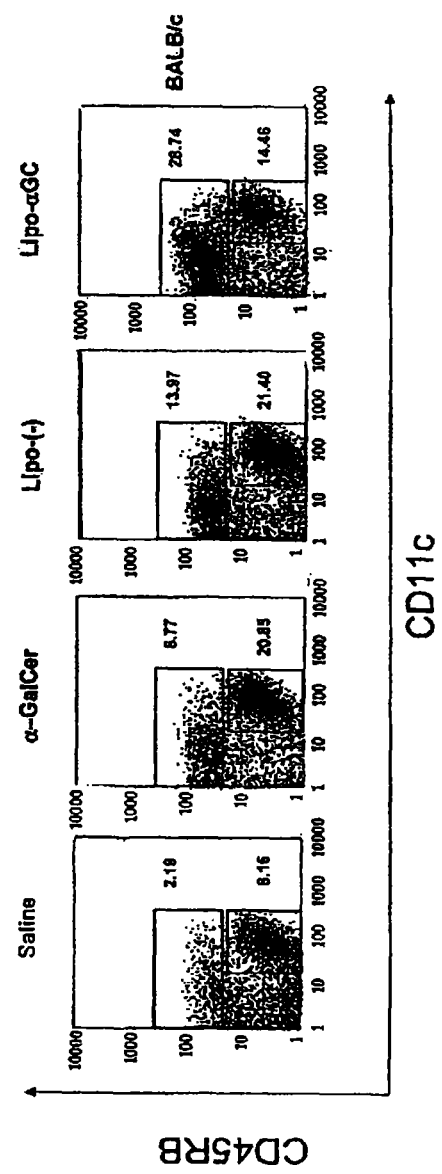
FIG. 12 shows the results of analyzing the cells by flow cytometry. Saline, α-GalCer, Lipo-(−) or Lipo-αGC was administered to BALB/c mice. After 3 days, the spleen cells were stained with anti-CD11c antibody and anti-CD45RB antibody.
Figure 13:
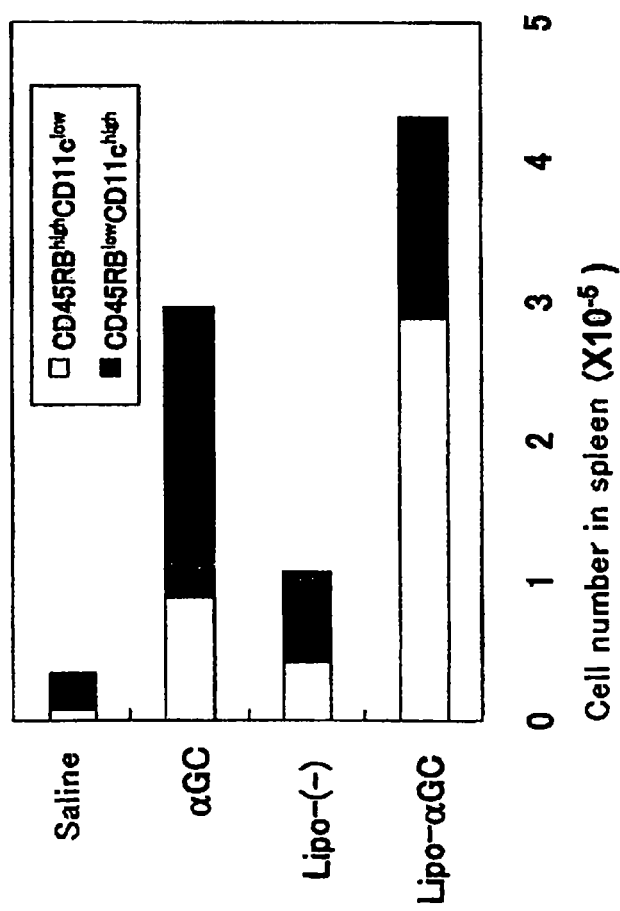
FIG. 13 shows the number of CD11c$^{low}$CD45RB$^{high}$ cells and the number of CD11c$^{high}$CD45RB$^{low}$ cells obtained by multiplying a cell number ratio obtained in flow cytometry memory analysis in FIG. 11 by the number of whole spleen cells.

4. Analysis of Dendritic Cells (DC) in Spleen of Mice Administered with Lipo-αGC 4-1. Analysis Using Flow Cytometry Saline, α-GalCer, Lipo-(−) or Lipo-αGC (2 µg/mouse) was intraperitoneally administered in BALB/c mice, and after 3 days, the spleen was removed. Collagenase D (1 mg/mL, Roche) was injected into the spleen, which was then incubated in the $CO_2$ incubator for 45 minutes. Subsequently, cells were collected from the spleen, suspended in 3 mL of HistoDenz (14.1%, SIGMA-Aldrich), and then the X-VIVO 15 medium (CAMBREX Bio Science Walkerville, Inc.) containing 50 µM 2-mercaptoethanol (2ME) was overlaid thereon. After centrifuging at 1,500 rpm for 5 minutes, the cells in the intermediate layer were collected. The cells were washed with the X-VIVO 15 medium containing 50 µm 2ME and 10% FCS, and suspended in phosphate buffered saline (PBS) containing 0.5% FCS. Biotinylated anti-CD3, -CD11b, -CD19, -CD49b, -Gr-1, -TER-119 and -B220 antibodies (all from BD Bioscience Pharmingen) were added to the cell suspension. The cells were incubated at 10° C. for 20 minutes, then washed once with PBS containing 0.5% FCS, and subsequently streptoavidin (SA)-conjugated magnetic beads (Miltenyi) were added thereto. The cells were incubated at 10° C. for 15 minutes, subsequently washed twice with PBS containing 0.5% FCS, and then magnetic microbead-negative cells were collected using a microbead separation column and a magnet (Miltenyi). The resulting cells were stained with PE-labeled anti-CD11c antibody (BD Bioscience Pharmingen) and APC-labeled anti-CD45RB antibody (BD Bioscience Pharmingen), and analyzed by flow cytometry. As a result, in the cells derived from the spleen of the mouse administered with Lipo-αGC, the ratio of $CD45RB^{high}CD11c^{low}$ cells was higher than the ratio of $CD45RB^{low}CD11c^{high}$ cells, while the ratio was reversed in the cells derived from the mice administered with saline, Lipo-(−) or α-GalCer (FIG. 12). The ratios were further compared in terms of cell number in the spleen. As a result, it was demonstrated that the number of the $CD45RB^{high}CD11c^{low}$ cells in the spleen of the mouse administered with Lipo-αGC increased about 3 times over the number of the corresponding cells in the spleen of the mouse administered with α-GalCer whereas conversely the number of the $CD45RB^{low}CD11c^{high}$ cells increased in the mouse administered with α-GalCer more than in the mouse administered with Lipo-αGC (FIG. 13).

Figure 14:
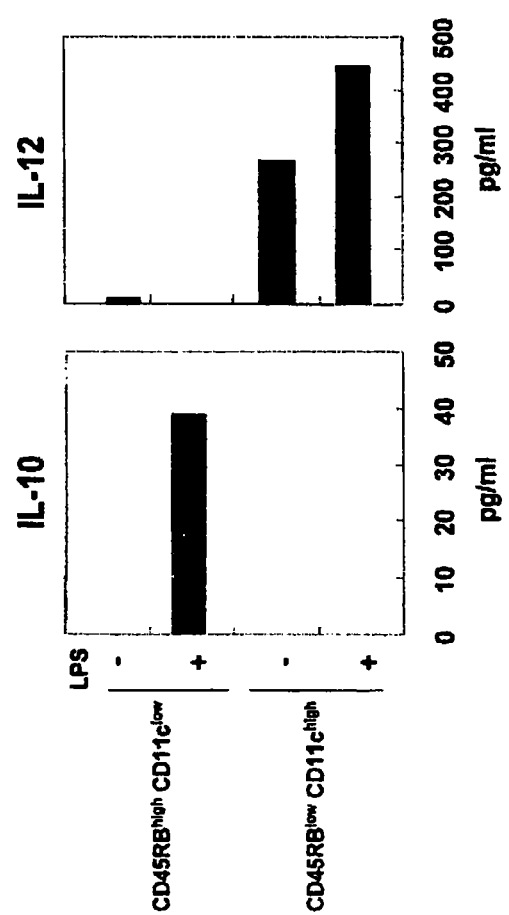
FIG. 14 shows the results of measuring cytokines in culture supernatants. Lipo-αGC was administered to BALB/c mouse. After 3 days, the CD11c$^{low}$CD45RB$^{high}$ cells and the CD11c$^{high}$CD45RB$^{low}$ cells separated from the spleen cells were stimulated with LPS. After 2 days, the culture supernatants were analyzed. The horizontal axis represents the concentration of the cytokine in the culture supernatant.

The $CD45RB^{high}CD11c^{low}$ cell is the cell group reported as a controllable dendritic cell and has the immunosuppressive function. Conversely, the $CD45RB^{low}CD11c^{high}$ cell is the dendritic cell which activates the T cell and has the immunostimulatory function. Thus, it was speculated that the immunosuppressive function of the NKT cells was brought by the increase in the number of the $CD45RB^{high}CD11c^{low}$ cell 4-2. Evaluation of Cytokine Production Ability The $CD45RB^{high}CD11c^{low}$ cell population and the $CD45RB^{low}CD11c^{high}$ cell population separated by the method described above were collected separately using the flow cytometry (FACS Vantage SE, BD Bioscience), and the cells at 1×10^5/200 µL of the medium were added into one well in the 96-well U bottom culture plate. The cells were cultured in the presence or absence of lipopolysaccharide (LPS; T3382, Sigma-Aldrich) at a final concentration of 1 µg/ml for 2 days. The levels of the cytokines IL-10 and IL-12 in the culture supernatant were measured by ELISA. As a result, IL-10 was detected and IL-12 was not detected in the culture supernatant of the $CD45RB^{high}CD11c^{low}$ cells stimulated with LPS whereas IL-12 was detected and IL-10 was not detected in the culture supernatants of the $CD45RB^{low}CD11c^{high}$ cells regardless of the presence or absence of LPS (FIG. 14).

4-3. Evaluation of T Cell Activation Ability

Figure 15:
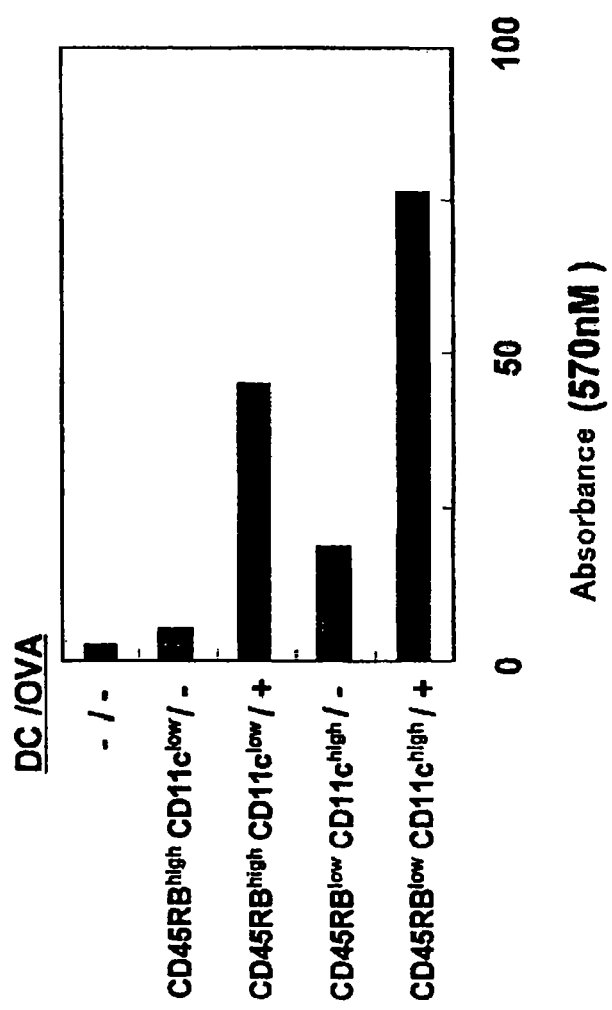
FIG. 15 shows the results of measuring the cell proliferation ability by MTT method. The CD11c$^{low}$CD45RB$^{high}$ cells or the CD11c$^{high}$CD45RB$^{low}$ cells pulsed with OVA$_{323-339}$ peptide were co-cultured with CD4$^+$ T cells derived from spleen of DO11.10 mouse, and after 48 hours, the cell proliferation ability was assayed. The horizontal axis represents the absorbance at a wavelength of 570 nm.
Figure 16:
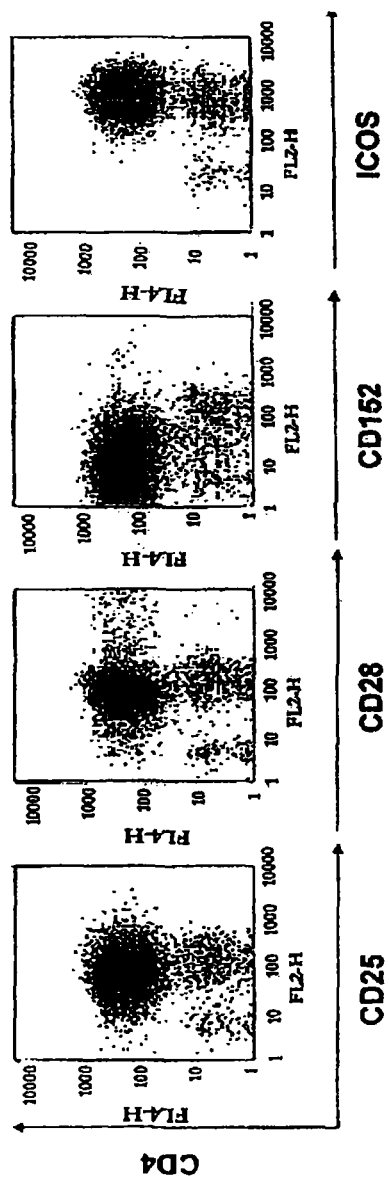
FIG. 16 shows the results of flow cytometry analysis using anti-CD4 antibody, and anti-CD25 antibody, anti-CD28 antibody, anti-CD152 antibody or anti-ICOS antibody. Cells proliferated by co-culturing the CD11c$^{low}$CD45RB$^{high}$ cells or the CD11c$^{high}$CD45RB$^{low}$ cells pulsed with OVA$_{323-339}$ peptide with the CD4$^+$ T cells derived from spleen of DO11.10 mouse were analyzed.
Figure 17:
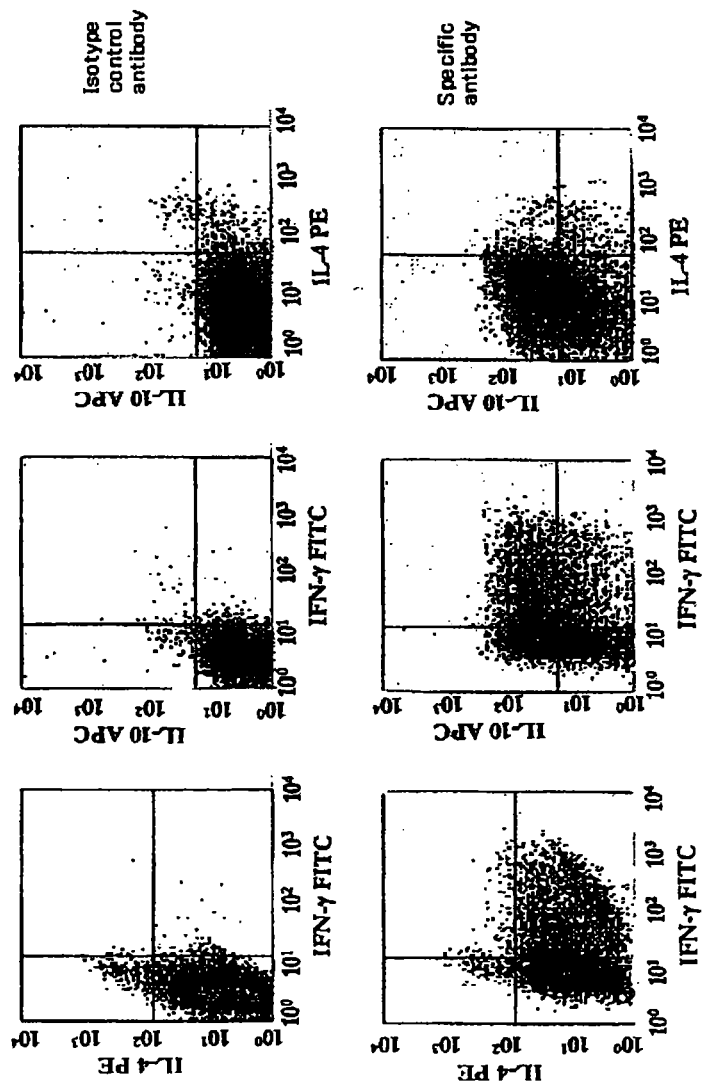
FIG. 17 shows the results of analyzing intracellular cytokine expression by flow cytometry. The cells proliferated by co-culturing the CD11c$^{low}$CD45RB$^{high}$ cells or the CD11c$^{high}$CD45RB$^{low}$ cells pulsed with OVA$_{323-339}$ peptide with the CD4$^+$ T cells derived from spleen of DO11.10 mouse were stimulated with PMA and ionomycin, and analyzed by flow cytometry. The upper panels represent intracellular staining patterns by the corresponding isotype control antibody. The lower panels represent the intracellular staining patterns by the cytokine-specific antibody.

The $CD45RB^{high}CD11c^{low}$ cells or the $CD45RB^{low}CD11c^{high}$ cells which are separated by the method described above 2. were added into one well of the 96-well U bottom culture plate at 1×10^4 cells/200 µL of the medium. The CD4+ T cells purified from the spleen of DO11.10 by the magnetic microbeads (Miltenyi) were added at 4×10^6 cells/200 µL of the medium thereto. The cells were cultured in the presence or absence of the $OVA_{323-339}$ peptide at a final concentration of 600 nM in the incubator containing 5% $CO_2$ at 37° C. After 48 hours, the proliferative response was assayed by MTT method (Promega #G4000). As a result, the CD4+ T cells stimulated with the $CD45RB^{high}CD11c^{low}$ cells and the OVA peptide exhibited the slightly inferior but significant proliferative response compared with the proliferative response induced by the $CD45RB^{low}CD11c^{high}$ cells (FIG. 15). The CD4+ T cells grown by the stimulation with the $CD45RB^{high}CD11c^{low}$ cells and the OVA peptide for 7 days were collected, and cultured with the $CD45RB^{high}CD11c^{low}$ cells or the $CD45RB^{low}CD11c^{high}$ cells newly separated/collected in the presence of OVA peptide for 7 days. This culture was performed once more, and on the 5th day, the cells in the culture were analyzed by flow cytometry. As a result, it was identified that the grown cell group was a nearly homogenous cell population with CD4+, CD25+, CD28+, CD152− and ICOS+ (FIG. 16). Subsequently, these cells at 5×10^5 were cultured in the presence of PMA at a final concentration of 50 ng/mL, 500 nM ionomycin and 2 µM Monensin (Sigma-Aldrich #M-5273) in the incubator containing 5% $CO_2$ at 37° C. for 4 hours. The cells were collected, suspended in 100 µL of a BD Cytofix/Cytoperm solution (BD Bioscience) and incubated at 4° C. for 15 minutes. The cells were washed with BD Perm/Wash (BD Bioscience), intracellularly stained with FITC-labeled anti-IFN-γ antibody, PE-labeled anti-IL-4 antibody (BD Bioscience Pharmingen) and APC-labeled anti-IL-10 antibody (BD Bioscience Pharmingen), and intracellular triple staining using fluorescence labeled isotype control antibodies was performed simultaneously (FIG. 17, upper panels). Then, the cells were analyzed by flow cytometry. As a result, in the cell group expressing the cytokines, it was identified that there was almost no cell expressing only IL-4 and the cell numbers were large in order of the cells expressing only IFNγ<the cells expressing both IL-10 and IFNγ<the cells expressing only IL-10 (FIG. 17, lower panels).

Example 6

Inhibitory Effect of Liposome Containing Allergen and Regulatory Cell Ligand on IgE Antibody Production 1. Preparation of Liposome Containing Ovalbumin and α-Galactosyl Ceramide L-α-Phosphatidylcholine, dioleoyl (DOPC; Wako Pure Chemical, 0.77 mg), 0.83 mg of cholesteryl 3β-N-(dimethylaminoethyl)carbonate hydrochloride (DC-Chol; Sigma-Aldrich) and 0.029 mg of 1,2-distearoyl-sn-glycero-3-phosethanolamine-N-[methoxy(polyethylene glycol)-2000] (ammonium salt; PEG-PE; AVANTI POLAR-LIPIDS) were dissolved in 250 µL of chloroform/methanol (1:1) solvent. α-Galactosyl ceramide (0.16 mg, supplied from RIKEN Research Center for Allergy and Immunology) was separately dissolved in 250 µL of chloroform/methanol (1:1) solvent. Both were mixed and evaporated using the evaporator, and subsequently dried overnight in the desiccator under vacuum. Subsequently, 200 µL of an aqueous solution containing 0.4 mg/mL of ovalbumin (OVA; Seikagaku Kogyo) was added thereto, the mixture was treated using the sonicator for 10 minutes, and passed through the membrane having a pore size of 0.22 µm for sterilization. Then, the particle sizes were selected by passing 25 times through LiposoFast-Basic extruder (Avestin Inc.) equipped with a polycarbonate membrane having a pore size of 100 nm. The OVA protein which had not been encapsulated in the liposome was eliminated by concentration of the liposomes in which OVA had been encapsulated using Amicon Ultra-4 centrifugation filter (PL-100) (Millipore) and washing with purified water, and finally the liposome was prepared into 800 µL of an aqueous solution with purified water. This aqueous solution containing the liposome composition (Lipo-αGC+OVA) was analyzed on SDS electrophoresis, and consequently it was identified that the concentration of the OVA protein was 50 µg/mL. All α-GalCer was supposed to be incorporated in the liposome membrane, and the final concentration of α-GalCer in the Lipo-αGC+OVA solution was rendered 200 µg/mL.

2. Induction of IL-10-Producing Regulatory CD4+ T Cells by Lipo-αGC+OVA

Figure 18:
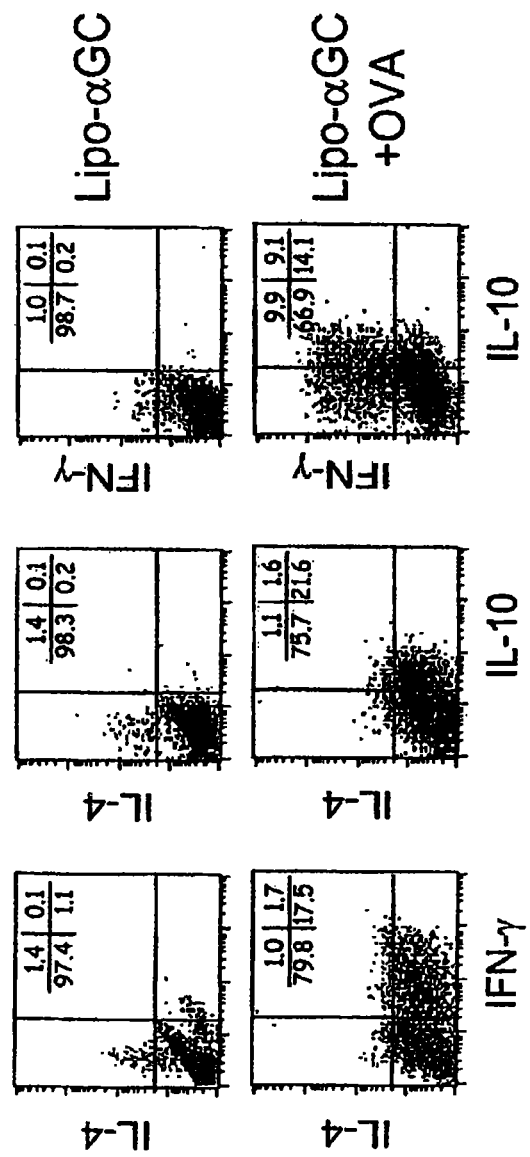
FIG. 18 shows the results of analyzing the intracellular cytokine expression by flow cytometry. The CD4$^+$ T cells from the spleen of BDF1 mouse administered with Lipo-αGC or Lipo-αGC+OVA were in vivo cultured with radiation irradiated spleen cells from the same BDF1 in the presence of OVA, and after 6 days, the cultured cells were stimulated with PMA and ionomycin. The upper panels represent the intracellular staining patterns of CD4$^+$ T cells from the spleen of the mouse administered with Lipo-αGC, and the lower panels represent the intracellular staining pattern of CD4$^+$ T cells from the spleen of the mouse administered with Lipo-αGC+OVA.

Lipo-αGC or Lipo-αGC+OVA (2 µg in terms of α-GalCer amount) was intraperitoneally administered in the BDF1 (C57BL/6×DBA/2 F1) mouse, after 7 days, the spleen was removed, and the CD4$^+$ T cells were prepared using the magnetic microbeads (Miltenyi). Subsequently, antigen presenting cells were prepared by irradiating spleen whole cells from the normal BDF1 mouse with radiation of 20 Gy. Then, 3 mL of the medium, the CD4$^+$ T cells at $1.5 \times 10^6$, the antigen presenting cells at $7.5 \times 10^6$ and the OVA protein at a final concentration of 100 µg/mL were added in one well of a 6-well U bottom culture plate, and cultured in the incubator containing 5% $CO_2$ at 37° C. for 6 days. Subsequently, the cells at $5 \times 10^5$ were cultured in the presence of PMA at a final concentration of 50 ng/mL, 500 nM of ionomycin and 2 µM Monensin (Sigma-Aldrich) in the incubator containing 5% $CO_2$ at 37° C. for 4 hours. The cells were collected, and stained with biotinylated anti-CD4 antibody and streptoavidin-Per CP-Cy5.5 (BD Bioscience). Subsequently, the cells were suspended in 100 µL of the BD Cytofix/Cytoperm solution (BD Bioscience) and incubated at 4° C. for 15 minutes. The cells were washed with BD Perm/Wash solution (BD Bioscience), then intracellularly stained with FITC-labeled anti-IFN-γ antibody, PE-labeled anti-IL-4 antibody (BD Bioscience Pharmingen) and APC-labeled anti-IL-10 antibody (BD Bioscience Pharmingen), and analyzed by flow cytometry (FIG. 18). As a result, in the CD4$^+$ T cells derived from the spleen of the mouse administered with Lipo-αGC without encapsulating OVA, 1.4% cells expressing only IL-4 and 1.1% cells expressing only IFNγ were detected but the CD4$^+$ regulatory T cell population expressing only IL-10 or both IFN-γ and IL-10 was scarcely detected. On the other hand, in the analysis of the CD4$^+$ T cells derived from the spleen of the mouse administered with Lipo-αGC+OVA, the helper T cell population expressing only IL-4 (1.0%) and only IFN-γ (9.9%), the IL-10-producing CD4$^+$ regulatory T cell population (14.1%) and the CD4$^+$ regulatory T cell population (9.1%) expressing both IL-10 and IFN-γ were detected. From the above results, it was suggested that the allergen-containing Lipo-αGC could in vivo differentiate and proliferate the allergen-specific CD4$^+$ regulatory T cells having the inhibitory effect on the IgE production.

3. Inhibitory Effect of Lipo-αGC+OVA on Secondary Antibody Response in Mice

Figure 19:
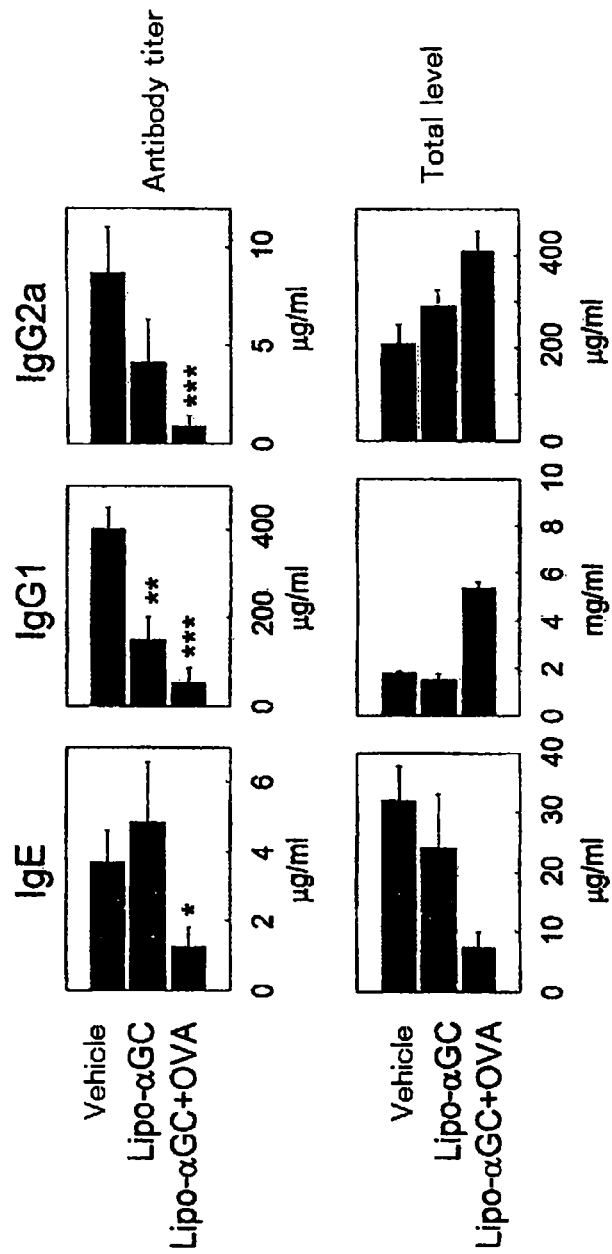
FIG. 19 shows antibody titers of anti-DNP-IgE, anti-DNP-IgG1, anti-DNP-IgG2a (upper panels), and levels of total IgE, total IgG1 and total IgG2a (lower panels) in blood. BDF1 mice were immunized with DNP-OVA and alum, on days 21, 28 and 35, a liposome alone (vehicle), Lipo-αGC or Lipo-αGC+OVA was administered, and then on day 42, the mice were boosted with DNP-OVA antigen alone. On day 48, the antibodies were assayed. * p<0.05,  p<0.005, * p<0.001

BDF1 mice were primarily immunized with DNP-OVA (0.1 µg) and aluminium hydroxide gel (2 mg). After 14 days, the antibody titers of anti-DNP-IgE antibody in blood were measured, and 3 groups (5 mice per group) were prepared so that the average antibody titers were equivalent among them. On 21, 28 and 35 days after the primary immunization, the liposome alone (vehicle), Lipo-αGC or Lipo-αGC+OVA at 2 µg in terms of α-GalCer amount was intraperitoneally administered. On the 42nd day after the primary immunization, the mice were boosted with DNP-OVA alone. On the 48th day, antibody titers of anti-DNP-IgE, anti-DNP-IgG1, anti-DNP-IgG2a, and the levels of total IgE, total IgG1 and total IgG2a in blood were measured by ELISA (FIG. 19). As a result, in the Lipo-αGC+OVA group, the antibody titers of anti-DNP-IgE, anti-DNP-IgG1 and anti-DNP-IgG2a were significantly suppressed. On the other hand, in the Lipo-αGC group containing no OVA, no significant suppression other than that in the antibody titer of anti-DNP-IgG1 was observed. From the above result, it was suggested that Lipo-αGC containing the allergen can suppress the secondary antibody response induced by the allergen.

4. Inhibitory Effect of Administration with α-Galactosyl Ceramide-Containing Liposome on In Vivo Production of Antigen Specific IgE Antibody The liposome alone, α-GC-liposome (α-GC: 2 µg/mouse) or α-GC-OVA-liposome (α-GC: 2 µg, OVA: 5 µg/mouse) was administered to BDF1 mice sensitized with DNP-OVA (0.1 µg) or DNP-KLH (1 µg) and aluminium hydroxide gel (2 mg), three times on the 21st, 28th and 35th days from the sensitization. The mice was boosted with DNP-OVA (0.1 µg) or DNP-KLH (1 µg) on the 42nd day from the sensitization. The amounts of anti-DNP IgE antibody, IgG1 antibody and IgG2a antibody in serum on the 49th day were measured by ELISA.

Figure 20:
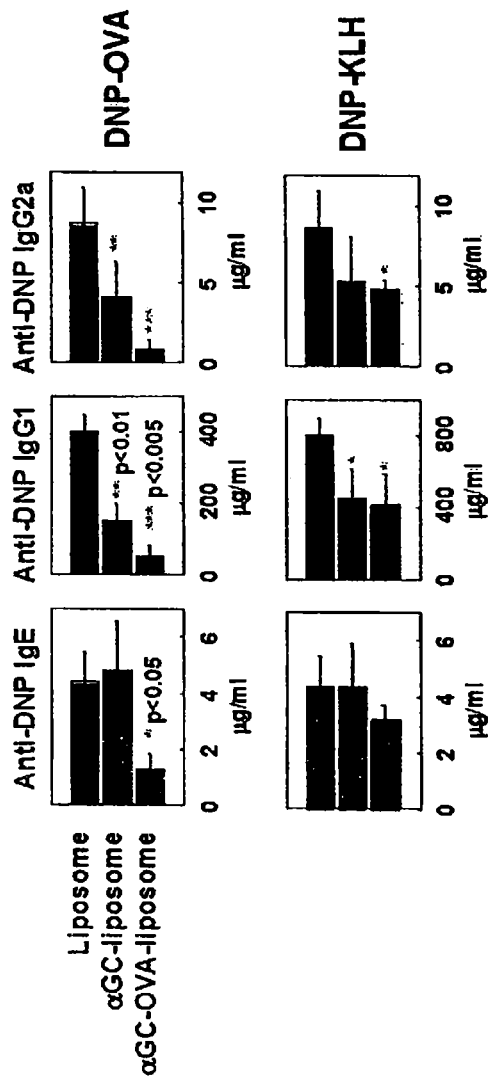
FIG. 20 is a view showing the concentrations of anti-DNP IgE, IgG1 and IgG2a in blood from mice administered with α-GC liposome or α-GC-OVA liposome, which had been sensitized with DNP-OVA or DNP-KLH.

As a result, in the group in which p60-GC-OVA-liposome had been added to the mice sensitized with DNP-OVA, the production of all IgE, IgG1 and IgG2a antibodies was significantly suppressed. However, in the group in which α-GC-liposome had been administered, the production of only IgG1 and igG2a antibodies was significantly suppressed, and the production of IgE antibody was not suppressed (FIG. 20).

From the above, it has been shown that the liposome containing α-GC and the allergen can be effective for the inhibition of the allergy caused by the allergen.

5. Inhibitory Effect of Administration with α-Galactosyl Ceramide-Containing Liposome on In Vivo Secondary and Tertiary IgE Antibody Production Saline, α-GC-liposome (α-GC: 2 µg/mouse), α-GC-OVA-liposome (α-GC: 2 µg, OVA: 5 µg/mouse) or the mixed solution of α-GC-liposome (α-GC: 2 µg/mouse) and OVA (5 µg/mouse) was intraperitoneally administered to BDF1 mice sensitized with OVA (0.1 µg) and aluminium hydroxide gel (2 mg), three times on the 21st, 28th and 35th day from the sensitization. The mice was boosted with OVA (0.1 µg) on the 52nd day after the sensitization, and boosted again on the 137th day. Blood samples were collected before the sensitization and on the 14th, 49th, 59th, 125th and 145th days after the sensitization, and the amounts of anti-OVA IgE antibody in serum were measured by ELISA.

Figure 21:
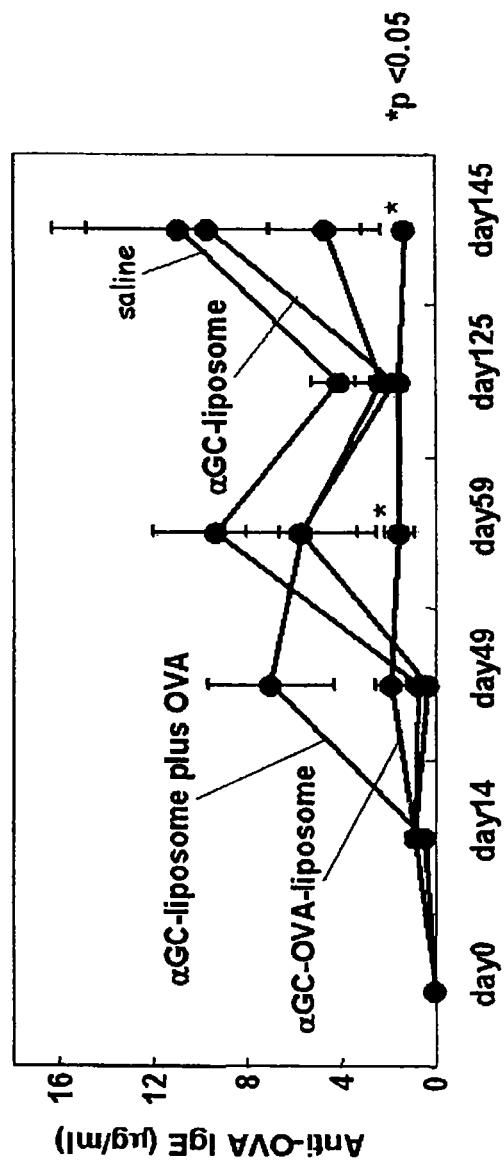
FIG. 21 is a view showing the concentrations of anti-OVA IgE in blood from mice administered with α-GC liposome or α-GC-OVA liposome or a mixed solution of α-GC liposome and OVA, which had been sensitized with DNP-OVA.

As a result, in the group in which α-GC-OVA-liposome had been administered, both secondary IgE antibody production after the first boosting and tertiary IgE antibody production after the second boosting were significantly suppressed, but in the group in which α-GC-liposome had been administered, no suppression was observed. In the group in which the mixed solution of α-GC-liposome and OVA had been administered, the increase of IgE antibody titer before the first boosting was identified, and the subsequent secondary and tertiary IgE productions were not significantly suppressed (FIG. 21).

From the above, it has been shown that the liposome containing α-GC and the allergen can significantly suppress the allergy caused by the allergen compared with the combination of the α-GC-containing liposome with the allergen.

INDUSTRIAL APPLICABILITY

The "liposome containing the regulatory cell ligand" of the present invention has the inhibitory actions on the activation action of the helper T cell and on the IgE antibody production by inducing the differentiation/proliferation and the activation of the regulatory cells. Thus, the liposome of the present invention is useful as the preventive agent and the therapeutic agent for the allergic diseases caused by the type I allergic response in which the IgE antibody is deeply involved, in particular atopic bronchial asthma, atopic dermatitis and allergic rhinitis such as pollinosis, and conjunctivitis.

The "α-galactosyl ceramide-containing liposome" is useful as the drug for autoimmune diseases and graft-versus-host disease because the liposome can inhibit the differentiation/proliferation of the pathogenic T cells by selectively augmenting the immunosuppressive function of the NKT cells.

In addition, no side effect is necessary to be concerned for the drug of the present invention because the drug retains the molecule selectively bound to the target cell and has the liposome including the regulatory cell ligand in the lipid membrane as the active ingredient.

The invention claimed is:

1. A pharmaceutical composition, comprising liposomes comprising KRN7000.

2. A method of preventing or treating graft versus host disease (GVHD), comprising administering the pharmaceutical composition of claim 1 to a subject in need of such prevention or treatment.

3. A method of preventing or treating rejection by a transplant patient, comprising administering the pharmaceutical composition of claim 1 to such patient.

4. A method of treating autoimmune diseases, comprising administering the pharmaceutical composition of claim 1 to a subject in need of such treatment.

5. A method of treating an allergic disease, comprising administering the pharmaceutical composition of claim 1 to a subject in need of such treatment.

6. The method of claim 5, wherein the allergic disease is selected from the group consisting of atopic bronchial asthma, allergic rhinitis, pollinosis, and atopic dermatitis.

* * * * *